United States Patent
Liang

(10) Patent No.: US 8,912,178 B2
(45) Date of Patent: *Dec. 16, 2014

(54) MTOR SELECTIVE KINASE INHIBITORS

(75) Inventor: Congxin Liang, Palm Beach Gardens, FL (US)

(73) Assignee: Xcovery Holdings Company, LLC, West Palm Beach, FL (US)

(*) Notice: Subject to any disclaimer, the term of this patent is extended or adjusted under 35 U.S.C. 154(b) by 3 days.

This patent is subject to a terminal disclaimer.

(21) Appl. No.: 13/698,501

(22) PCT Filed: May 18, 2011

(86) PCT No.: PCT/US2011/036968
§ 371 (c)(1),
(2), (4) Date: Nov. 16, 2012

(87) PCT Pub. No.: WO2011/146594
PCT Pub. Date: Nov. 24, 2011

(65) Prior Publication Data
US 2013/0072481 A1    Mar. 21, 2013

Related U.S. Application Data

(60) Provisional application No. 61/346,278, filed on May 19, 2010.

(51) Int. Cl.
*A61K 31/535* (2006.01)
*C07D 413/00* (2006.01)
*C07D 487/04* (2006.01)

(52) U.S. Cl.
CPC .................................... *C07D 487/04* (2013.01)
USPC ........................................ 514/234.2; 544/118

(58) Field of Classification Search
None
See application file for complete search history.

(56) References Cited

U.S. PATENT DOCUMENTS 8,586,582 B2 * 11/2013 Liang et al. ................. 514/234.2
2011/0281857 A1 * 11/2011 Liang et al. ................. 514/230.5

FOREIGN PATENT DOCUMENTS

WO    WO-2008018426 A1    2/2008
WO    WO-2010056320 A2    5/2010

OTHER PUBLICATIONS

Mukaiyama (Tetrahedron 55 (1999) 8609-8670)).*
Journal of Medicinal Chemistry 2009, vol. 52, pp. 5013-5016.
Bioorganic & Medicinal Chemistry Letters 2009, vol. 19. pp. 6830-6835.
Cancer Research 2009, vol. 69, No. 15, pp. 6232-6240.
Bioorganic & Medicinal Chemistry Letters, Jan. 2010, vol. 20, pp. 636-639.
International Search Report of PCT/US2011/036968.

* cited by examiner

*Primary Examiner* — Jeffrey S. Lundgren
*Assistant Examiner* — William Lee
(74) *Attorney, Agent, or Firm* — Edwards Wildman Palmer LLP; Jeffrey D. Hsi

(57) ABSTRACT

The 4-urea-phenyl substituted 6-morpholin-4-yl-pyrazolo[3,4-d]pyrimidine derivatives are potent and selective inhibitors of mTOR kinase and are useful in treating disorders related to abnormal mTOR activities such as cancer, immune disorders, cardiovascular disease, ocular disease, viral infection, inflammation, metabolism/endocrine disorders and neurological disorders.

11 Claims, No Drawings

MTOR SELECTIVE KINASE INHIBITORS

CROSS-REFERENCE TO RELATED APPLICATIONS

This application is the national phase under 35 U.S.C. §371 of PCT International Application No. PCT/US2011/036968, filed May 18, 2011 which claims the benefit of U.S. Provisional Patent Application No. 61/346,278, filed May 19, 2010, the entire contents of the aforementioned applications are hereby incorporated herein by reference.

TECHNICAL FIELD OF THE INVENTION

This invention relates to novel 4-urea-phenyl substituted 6-morpholin-4-yl-pyrazolo[3,4-d]pyrimidine derivatives, their salts, solvates, hydrates and polymorphs thereof. The invention also provides compositions comprising a compound of this invention and the use of such compositions in methods of treating diseases and conditions associated with kinase modulation, especially the mTOR kinase.

BACKGROUND OF THE INVENTION

The mammalian target of rapamycin (mTOR) pathway is considered a major regulator of cell growth (Guertin, D. A., and Sabatini, D. M. *Cancer Cell* 2007, 12, 9). The mTOR serine/threonine kinase is the founding component of the pathway and the catalytic subunit of two functionally distinct protein complexes, mTORC1 and mTORC2. mTORC1 contains the large protein Raptor, as well as mLST8/GβL and PRAS40, whereas mTORC2 is defined by the protein Rictor and also includes Sin1, Protor, and mLST8/GβL. Growth factors, such as insulin and IGF, activate both complexes, and they are important downstream effectors of the PI3K/PTEN signaling network. Additionally, the availability of nutrients, like amino acids and glucose, regulates mTORC1. Many insights into mTOR signaling have come from investigations into the mechanism of action of rapamycin, a bacterially produced macrolide inhibitor of mTOR that has diverse clinical applications as an anti-fungal, immunosuppressant, and anti—Cancer drug. Rapamycin acts through an unusual allosteric mechanism that requires binding to its intracellular receptor, FKBP12, for inhibition of its target. Under acute treatment, rapamycin is thought to selectively inhibit mTORC1, which is often referred to as the rapamycin—Sensitive complex. Conversely, mTORC2 is considered rapamycin-insensitive, although its assembly can be inhibited by prolonged rapamycin treatment in some cell types. Because of its perceived potency and selectivity, rapamycin is commonly used in research experiments as a test of the involvement of mTORC1 in a particular process.

Two downstream mTORC1 substrates that were identified, in part, by their sensitivity to rapamycin are the S6 kinases (S6K1 and S6K2) and the translational inhibitor 4E-BP1. Both proteins mediate important links between mTORC1 and the cell growth machinery, largely through their influence on cap-dependent translation. All nuclear-encoded mRNAs possess a 5',7-methyl guanosine cap, which is recognized and bound by the small protein eIF-4E. Under growth-promoting conditions, eIF-4E also associates with the large scaffolding protein eIF-4G, the eIF-4A helicase, and the eIF-4B regulatory protein, together forming the eIF-4F complex. This complex, in conjunction with the eIF3 pre-initiation complex, delivers the mRNA to the 40 S ribosomal subunit and primes the translational apparatus. 4E-BP1 interferes with this process by binding to eIF-4E and preventing the formation of a functional eIF-4F complex. However, its ability to do this is blocked by phosphorylation at four sites, two of which are considered rapamycin—Sensitive. S6K1 also plays a role in regulating translational initiation by phosphorylating the S6 protein of the 40 S ribosomal subunit and by stimulating eIF-4A helicase activity.

Despite the connections of mTORC1 to the translational machinery, the effects of rapamycin on mammalian cell growth and proliferation are, oddly, less severe than its effects in yeast. In *Saccharomyces cerevisiae*, rapamycin treatment induces a starvation-like state that includes a severe G1/S cell cycle arrest and suppression of translation initiation to levels below 20% of non-treated cells. Moreover, in yeast rapamycin strongly promotes induction of autophagy (self-eating), a process by which cells consume cytoplasmic proteins, ribosomes, and organelles, such as mitochondria, to maintain a sufficient supply of amino acids and other nutrients. The effects of rapamycin in mammalian cells are similar to those in yeast, but typically much less dramatic and highly dependent on cell type. For instance, rapamycin only causes cell cycle arrest in a limited number of cell types and has modest effects on protein synthesis. Moreover, rapamycin is a relatively poor inducer of autophagy, and it is often used in combination with LY294002, an inhibitor of PI3K and mTOR. These inconsistent effects may explain why, despite high expectations, rapamycin has had only limited success as a clinical anti—Cancer therapeutic.

Recently, it was reported that highly potent and selective ATP—Competitive mTOR inhibitors, that directly inhibits both complexes, impair cell growth and proliferation to a far greater degree than rapamycin (Thoreen et al. *J. Biological Chem.* 2009, 284, 8023. Feldman et al. *PLoS Biology* 2009, 7, 731. Garcia-Martinez et al. *Biochem. J.* 2009, 421, 29. Yu et al. *Cancer Res,* 2010, 70, 621). These effects are independent of mTORC2 inhibition and are instead because of suppression of rapamycin-resistant functions of mTORC1 that are necessary for cap-dependent translation and suppression of autophagy. These effects are at least partly mediated by mTORC1-dependent and rapamycin-resistant phosphorylation of 4E-BP1. These findings challenge the assumption that rapamycin completely inhibits mTORC1 and indicate that direct inhibitors of mTORC1 kinase activity may be more successful than rapamycin at inhibiting tumors that depend on mTORC1.

Previously, we disclosed that 6-morpholin-4-yl-pyrazolo[3,4-d]pyrimidine derivatives (Formula I) are potent and selective PI3K/mTOR inhibitors (U.S. provisional application Ser. No. 61/199,019 and 61/214,828). In general, these compounds inhibit both PI3K (particularly the α, β, δ isoforms) and mTOR, displaying little or no selectivity among these kinases.

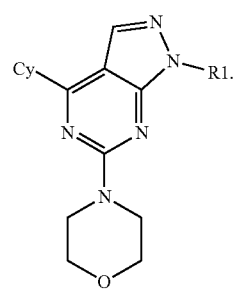

I

In this invention, we discovered that the 4-urea-phenyl substituted 6-morpholin-4-yl-pyrazolo[3,4-d]pyrimidine derivatives (Cy=4-urea-phenyl) are potent and selective mTOR kinase inhibitors with much less PI3K inhibitory activities. Giving the exciting anti-tumor activities, at least in pre—Clinical studies, of mTOR kinase inhibitors as discussed above, these novel compounds may also have potential in treating diseases mediated by mTOR such as cancer, immune disorders, cardiovascular disease, ocular disease, viral infection, inflammation, metabolism/endocrine disorders and neurological disorders.

SUMMARY OF THE INVENTION

The invention relates to 4-urea-phenyl substituted 6-morpholin-4-yl-pyrazolo[3,4-d]pyrimidine derivative compounds, compositions comprising the compounds, and methods of using the compounds and compound compositions. The compounds and compositions comprising them are useful for treating or preventing disease or disease symptoms, including those mediated by or associated with mTOR activities.

One aspect is a compound of Formula II:

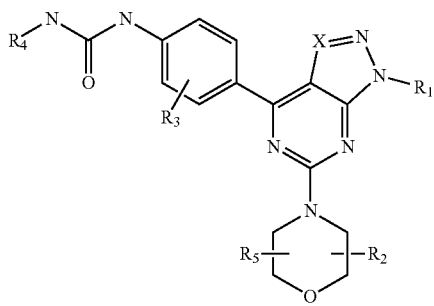

or a salt thereof; or a prodrug, or a salt of a prodrug thereof; or a hydrate, solvate, or polymorph thereof; wherein X is N or CR'; $R_1$, $R_2$, $R_3$, $R_5$ and R' are independently hydrogen, alkyl, cycloalkyl, or heterocyclo, each optionally substituted with $Z_1$, $Z_2$ and $Z_3$; each $R_4$ is independently alkyl, aryl, cycloalkyl, heteroaryl or heterocyclo, each optionally substituted with $Z_1$, $Z_2$ and $Z_3$; wherein each $R_2$ and $R_5$ together with the atom(s) that each is respectively attached to can form a cyclo or heterocyclo structure;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; (ii) a group (i) which is substituted by one or more groups selected from alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; or (iii) a group (i) or (ii) which is substituted by one or more of the following groups (2) to (13);
(2) —OH or —$OZ_{16}$;
(3) —SH or —$SZ_{16}$;
(4) —$C(O)_2H$, —$C(O)_qZ_{16}$, —$C(O)NZ_{17}Z_{18}$, —C(O)C(O)$NZ_{17}Z_{18}$, or —O—$C(O)_qZ_{16}$, where q is 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—N($Z_{18}$)—$Z_5$—$NZ_{19}Z_{20}$;
(11) oxo;
(12) —O—C(O)—$Z_{16}$;
(13) —P(O)($OZ_{17}$)($OZ_{18}$) or —O—P(O)($OZ_{17}$)($OZ_{18}$);
(14) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently
(1) a single bond;
(2) —$Z_{11}$—$S(O)_q$—$Z_{12}$—;
(3) —$Z_{11}$—C(O)—$Z_{12}$—;
(4) —$Z_{11}$—O—$Z_{12}$—;
(5) —$Z_{11}$—S—$Z_{12}$—;
(6) —$Z_{11}$—O—C(O)—$Z_{12}$—; or
(7) —$Z_{11}$—C(O)—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(1) hydrogen;
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —C(O)C(O)$NZ_{17}Z_{18}$, or —O—$C(O)_qZ_{21}$,
where q is 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—N($Z_{18}$)—$Z_5$—$NZ_{19}Z_{20}$;
(11) oxo;
(12) —O—C(O)—$Z_{21}$;
(13) —P(O)($OZ_{17}$)($OZ_{18}$) or —O—P(O)($OZ_{17}$)($OZ_{18}$);
(14) alkyl;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{22}$ is independently is,
(1) hydrogen;
(2) —OH or —$OZ_{21}$;
(3) —SH or —$SZ_{21}$;
(4) —$C(O)_2H$, $C(O)_qZ_{21}$, —$C(O)NZ_{21}Z_{21}$, —$C(O)C(O)NZ_{21}Z_{21}$, or —O—$C(O)_qZ_{21}$, where q is 1 or 2;
(5) —$SO_3H$, —$S(O)_qZ_{21}$, or —$S(O)_qNZ_{21}Z_{21}$;
(6) halo;
(7) cyano;
(8) nitro;
(9) —$Z_4$—$NZ_{21}Z_{21}$;
(10) —$Z_4$—$N(Z_{21})$—$Z_5$—$NZ_{21}Z_{21}$;
(11) oxo;
(12) —O—C(O)—$Z_{21}$;
(13) —$P(O)(OZ_{17})(OZ_{18})$ or —$OP(O)(OZ_{17})(OZ_{18})$;

where $Z_{17}$, $Z_{18}$, $Z_{19}$ or $Z_{20}$ may be substituted with 1, 2, or 3 independent $Z_{22}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$.

The compounds of this invention, and compositions comprising them, are useful for treating or lessening the severity of mTOR modulated diseases, disorders, or symptoms thereof.

In another aspect, the invention relates to a method of treating a disease or disease symptom in a subject in need thereof including administering to the subject an effective amount of a compound of any formulae herein, or pharmaceutical salt, solvate or hydrate thereof (or composition thereof). The disease or disease symptom can be any of those modulated by mTOR. The disease or disease symptom can be, for example, cancer, immune disorders, cardiovascular disease, ocular disease, viral infection, inflammation, metabolism/endocrine disorders and neurological disorders.

DETAILED DESCRIPTION OF THE INVENTION

Definitions

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate) analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.;

Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive). The term "arylalkyl" refers to a moiety in which an alkyl hydrogen atom is replaced by an aryl group. The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —(CH$_2$)$_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. In aspects, functional group delineated herein, e.g., alkyl, alkenyl, alkynyl, cycloalkyl, cycloalkenyl, aryl, heterocyclyl, or heteroaryl, can be substituted with a substituent (e.g., those listed below). Suitable substituents include, without limitation, halogen, CN, NO$_2$, OR$^{15}$, SR$^{15}$, S(O)$_2$OR$^{15}$, NR$^{15}$R$^{16}$, C$_1$—C$_2$ perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)R$^{17}$, NR$^{15}$C(O)R$^{17}$, S(O)R$^{17}$, S(O)$_2$R$^{17}$, R$^{16}$, oxo, C(O)R$^{16}$, C(O)(CH$_2$)nOH, (CH$_2$)nOR$^{15}$, (CH$_2$)nC(O)NR$^{15}$R$^{16}$, NR$^{15}$S(O)$_2$R$^{17}$, where n is independently 0-6 inclusive. Each R$^{15}$ is independently hydrogen, C$_1$-C$_4$ alkyl or C$_3$-C$_6$ cycloalkyl. Each R$^{16}$ is independently hydrogen, alkenyl, alkynyl, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, NH$_2$, C$_1$-C$_4$ alkylamino, C$_1$-C$_4$ dialkylamino, C$_1$-C$_2$ perfluoroalkyl, C$_1$-C$_2$ perfluoroalkoxy, or 1,2-methylenedioxy.

The term "oxo" refers to an oxygen atom, which forms a carbonyl when attached to carbon, an N-Oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

One aspect is a compound of Formula II:

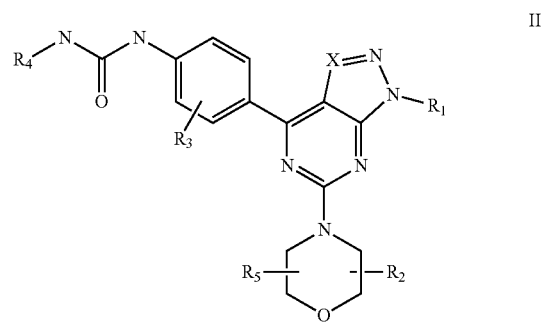

or a salt thereof; or a prodrug, or a salt of a prodrug thereof; or a hydrate, solvate, or polymorph thereof; wherein X is N or CR'; R$_1$, R$_2$, R$_3$, R$_5$ and R' are independently hydrogen, alkyl, cycloalkyl, or heterocyclo, each optionally substituted with Z$_1$, Z$_2$ and Z$_3$; each R$_4$ is independently alkyl, aryl, cycloalkyl, heteroaryl or heterocyclo, each optionally substituted with Z$_1$, Z$_2$ and Z$_3$; wherein each R$_2$ and R$_5$ together with the atom(s) that each is respectively attached to can form a cyclo or heterocyclo structure;

Z$_1$, Z$_2$ and Z$_3$ are each independently:
(1) hydrogen or Z$_6$, where Z$_6$ is (i) alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

(ii) a group (i) which is substituted by one or more groups selected from alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl; or (iii) a group (i) or (ii) which is substituted by one or more of the following groups (2) to (13);

(2) —OH or —$OZ_{16}$;
(3) —SH or —$SZ_{16}$;
(4) —$C(O)_2H$, $C(O)_qZ_{16}$, —$C(O)NZ_{17}Z_{18}$, —$C(O)C(O)NZ_{17}Z_{18}$, or —O—$C(O)_qZ_{16}$, where q is 1 or 2;
(5) —$SO_3H$, —$S(O)_qZ_{16}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5$—$NZ_{19}Z_{20}$;
(11) oxo;
(12) —O—C(O)—$Z_{16}$;
(13) —$P(O)(OZ_{17})(OZ_{18})$ or —O—$P(O)(OZ_{17})(OZ_{18})$;
(14) any two of $Z_1$, $Z_2$, and $Z_3$ may together be alkylene, alkenylene, aryl, heteroaryl, or heterocyclo completing a 3- to 8-membered saturated or unsaturated ring together with the atoms to which they are attached;

$Z_4$ and $Z_5$ are each independently
(1) a single bond;
(2) —$Z_{11}$—$S(O)_q$—$Z_{12}$—;
(3) —$Z_{11}$—C(O)—$Z_{12}$—;
(4) —$Z_{11}$—O—$Z_{12}$—;
(5) —$Z_{11}$—S—$Z_{12}$—;
(6) —$Z_{11}$—O—C(O)—$Z_{12}$—; or
(7) —$Z_{11}$—C(O)—O—$Z_{12}$;

$Z_{11}$ and $Z_{12}$ are each independently
(1) a single bond;
(2) alkylene;
(3) alkenylene; or
(4) alkynylene;

each $Z_{16}$ is independently alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl, each optionally substituted with one or more of the following groups:
(1) hydrogen;
(2) —OH or —$OZ_{21}$;
(3) —SH or —$SZ_{21}$;
(4) —$C(O)_2H$, $C(O)_qZ_{21}$, —$C(O)NZ_{17}Z_{18}$, —$C(O)C(O)NZ_{17}Z_{18}$, or —O—$C(O)_qZ_{21}$, where q is 1 or 2;
(5) —$SO_3H$, —$S(O)_qZ_{21}$, or —$S(O)_qNZ_{17}Z_{18}$;
(6) halo;
(7) cyano;
(8) nitro;
(9) —$Z_4$—$NZ_{17}Z_{18}$;
(10) —$Z_4$—$N(Z_{18})$—$Z_5NZ_{19}Z_{20}$;
(11) oxo;
(12) —O—C(O)—$Z_{21}$;
(13) —$P(O)(OZ_{17})(OZ_{18})$ or —O—$P(O)(OZ_{17})(OZ_{18})$;
(14) alkyl;

each $Z_{17}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{18}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{19}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{20}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{21}$ is independently hydrogen, alkyl, alkenyl, alkynyl, cycloalkyl, cycloalkylalkyl, cycloalkenyl, cycloalkenylalkyl, aryl, heteroaryl, aralkyl, heteroarylalkyl, alkylaryl, cycloalkylaryl, heterocyclo, or heterocycloalkyl;

each $Z_{22}$ is independently is,
(1) hydrogen;
(2) —OH or —$OZ_{21}$;
(3) —SH or —$SZ_{21}$;
(4) —$C(O)_2H$, $C(O)_qZ_{21}$, —$C(O)NZ_{21}Z_{21}$, —$C(O)C(O)NZ_{21}Z_{21}$, or —O—$C(O)_qZ_{21}$, where q is 1 or 2;
(5) —$SO_3H$, —$S(O)_qZ_{21}$, or —$S(O)_qNZ_{21}Z_{21}$;
(6) halo;
(7) cyano;
(8) nitro;
(9) —$Z_4$—$NZ_{21}Z_{21}$;
(10) —$Z_4$—$N(Z_{21})$—$Z_5$—$NZ_{21}Z_{21}$;
(11) oxo;
(12) —O—C(O)—$Z_{21}$;
(13) —$P(O)(OZ_{17})(OZ_{18})$ or —O—$P(O)(OZ_{17})(OZ_{18})$;

where $Z_{17}$, $Z_{18}$, $Z_{19}$ or $Z_{20}$ may be substituted with 1, 2, or 3 independent $Z_{22}$;

where $Z_{17}$ and $Z_{18}$, or $Z_{19}$ and $Z_{20}$, together with the nitrogen atom to which they are attached may be a heterocycle which is unsubstituted or substituted with 1, 2, or 3 independent $Z_{22}$; and where any two of $Z_{18}$, $Z_{19}$ or $Z_{20}$ together with the nitrogen atoms to which they are attached may be a 3- to 12-membered saturated or unsaturated mono-, bi-, or tri-heterocyclic ring which is unsubstituted or substituted with 1, 2, or 3 independent $Z_{22}$.

Another aspect is a compound of formula II, wherein the compound is of formulae IIa:

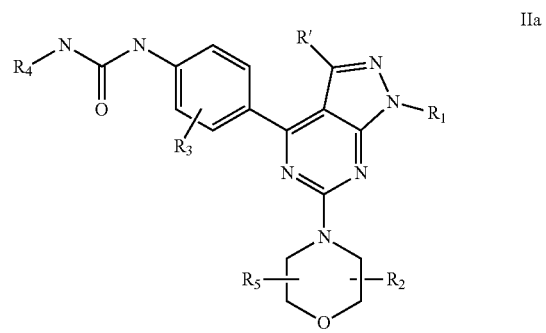

IIa wherein $R_1$, $R_2$, $R_3$, $R_5$, and R' are independently hydrogen, alkyl, cycloalkyl, or heterocyclo, each optionally substituted with $Z_1$, $Z_2$ and $Z_3$; and each $R_4$ is independently alkyl, aryl, cycloalkyl, heteroayl or heterocyclo, each optionally substituted with $Z_1$, $Z_2$ and $Z_3$; wherein each $R_2$ and $R_5$ together with the atom(s) that each is respectively attached to can form a cyclo or heterocyclo structure.

Another aspect is a compound of formula II, wherein the compound is of formulae IIb:

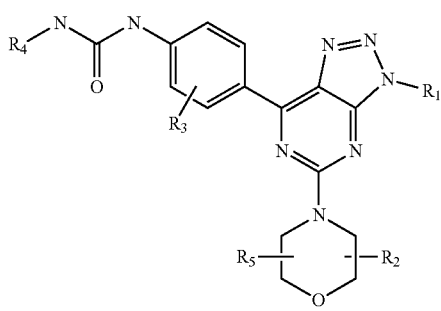

wherein $R_1$, $R_2$, $R_3$, and $R_5$ are each independently hydrogen, alkyl, cycloalkyl, or heterocyclo, each optionally substituted with $Z_1$, $Z_2$ and $Z_3$; and each $R_4$ is independently alkyl, aryl, cycloalkyl, heteroayl or heterocyclo, each optionally substituted with $Z_1$, $Z_2$ and $Z_3$; wherein each $R_2$ and $R_5$ together with the atom(s) that each is respectively attached to can form a cyclo or heterocyclo structure.

Another aspect is a compound of any of the formulae herein, wherein $R_2$ and $R_5$ together with the atoms to which they are attached form a heterocycloalkyl.

Another aspect is a compound of any of the formulae herein, wherein $R_1$ is alkyl optionally substituted with $Z_1$, $Z_2$ and $Z_3$.

Another aspect is a compound of any of the formulae herein, wherein $R_1$ is alkyl substituted with $Z_1$, $Z_2$ and $Z_3$.

Another aspect is a compound of any of the formulae herein, wherein $R_1$ is heterocyclyl optionally substituted with $Z_1$, $Z_2$ and $Z_3$.

Another aspect is a compound of any of the formulae herein, wherein $R_4$ is alkyl.

Another aspect is a compound of any of the formulae herein, wherein $R_4$ is aryl optionally substituted with $Z_1$, $Z_2$ and $Z_3$.

Another aspect is a compound of any of the formulae herein, wherein $R_4$ is aryl substituted with —C(O)$Z_{16}$.

Another aspect is a compound of any of the formulae herein, wherein $Z_{16}$ is alkyl.

Another aspect is a compound of any of the formulae herein, wherein $R_4$ is aryl substituted with heterocyclyl.

Another aspect is a compound of any of the formulae herein, wherein $R_1$ is alkyl optionally substituted with $Z_1$, $Z_2$ and $Z_3$;

$R_4$ is independently alkyl.

Another aspect is a compound of any of the formulae herein, wherein $R_1$ is alkyl optionally substituted with $Z_1$, $Z_2$ and $Z_3$;

$R_4$ is aryl optionally substituted with $Z_1$, $Z_2$ and $Z_3$.

Another aspect is a compound of any of the formulae herein, wherein; $R_1$ is heterocyclyl optionally substituted with $Z_1$, $Z_2$ and $Z_3$;

$R_4$ is alkyl optionally substituted with $Z_1$, $Z_2$ and $Z_3$.

Another aspect is a compound of any of the formulae herein, wherein; $R_1$ is cycloalkyl optionally substituted with $Z_1$, $Z_2$ and $Z_3$;

$R_4$ is alkyl optionally substituted with $Z_1$, $Z_2$ and $Z_3$.

Another aspect is a compound of any of the formulae herein, wherein X is CH.

In one aspect, the compound is a compound of Table 1. In one aspect, the compound is a compound of Table 2. In one aspect, the compound is a compound of Table 3.

Representative compounds of the invention are depicted in Tables 1, 2 and 3. The structures in Tables and the schemes herein contain certain —NH—, —NH$_2$ (amino) and —OH (hydroxyl) groups where the corresponding hydrogen atom (s) do not explicitly appear; however they are to be read as —NH—, —NH$_2$ or —OH as the case may be.

TABLE 1

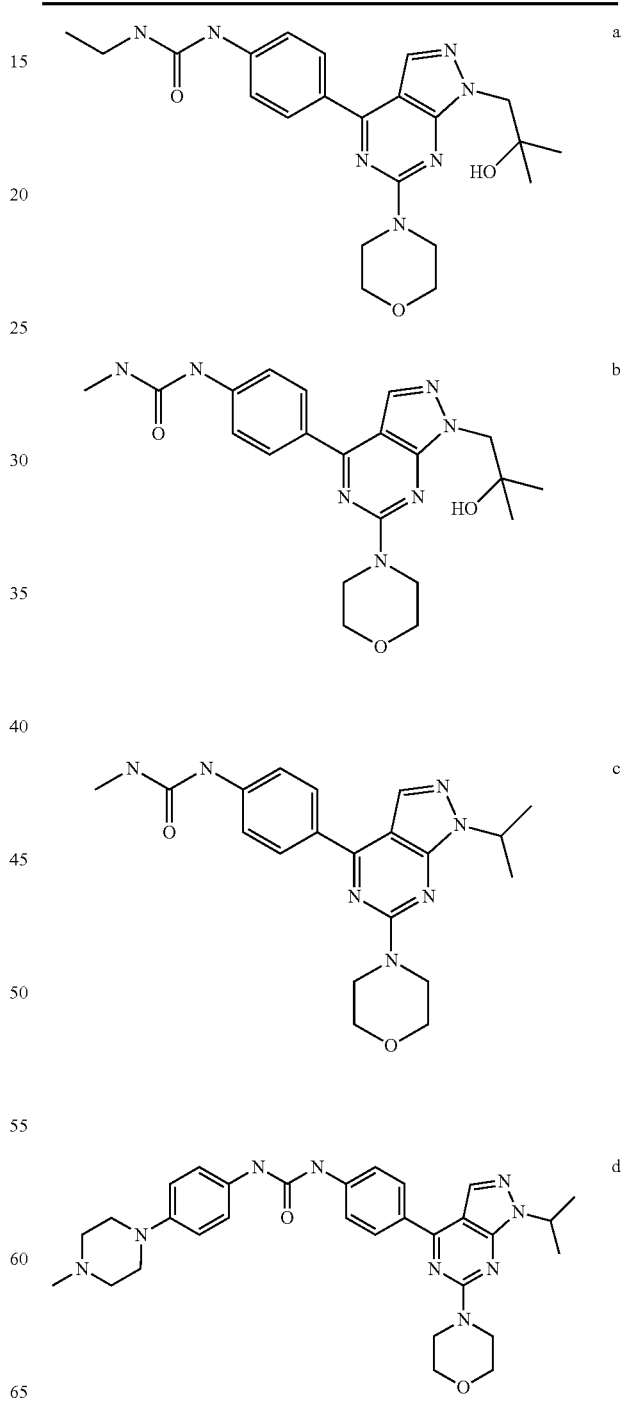

TABLE 1-continued
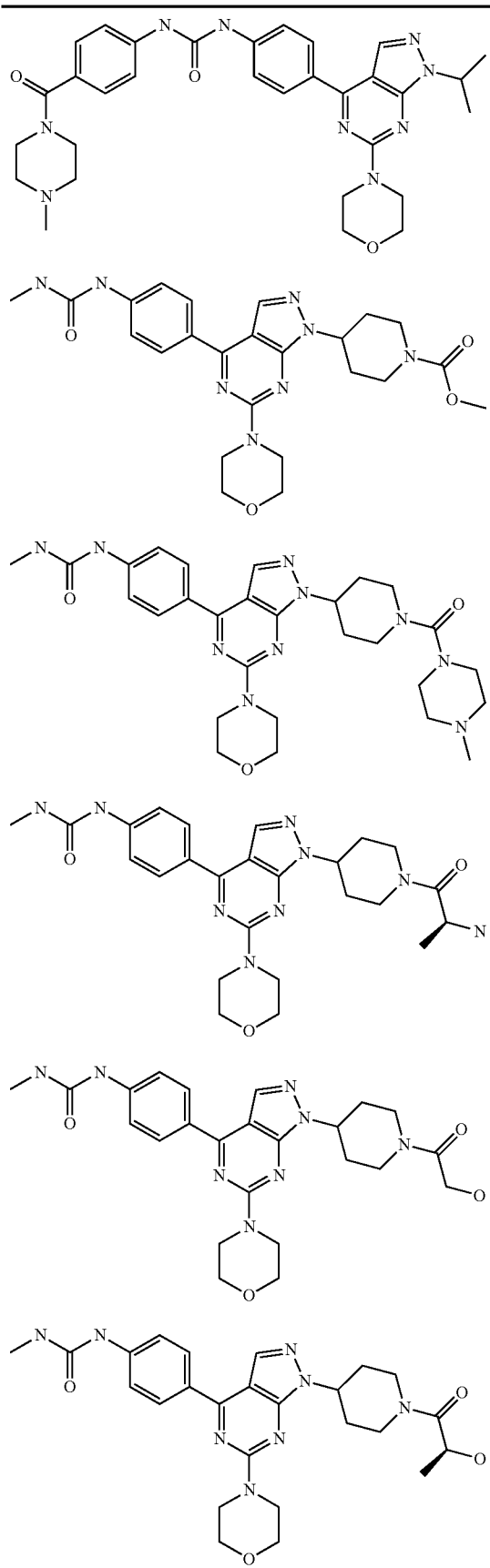
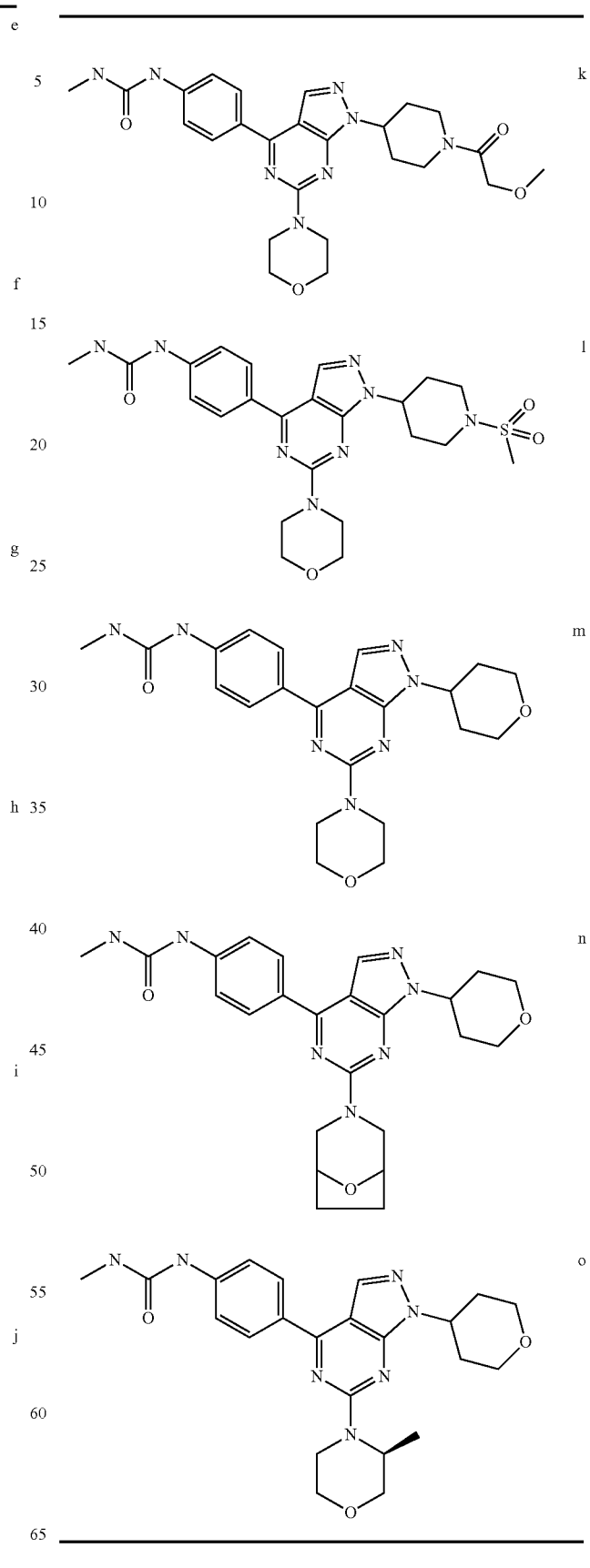

TABLE 2

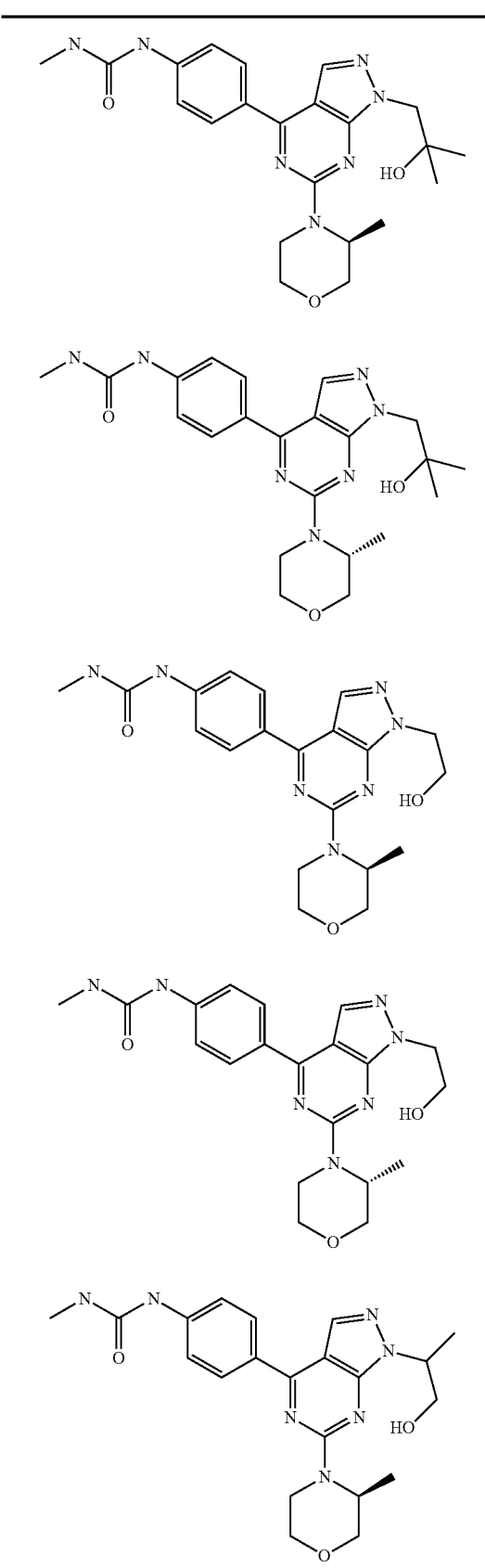

TABLE 2-continued

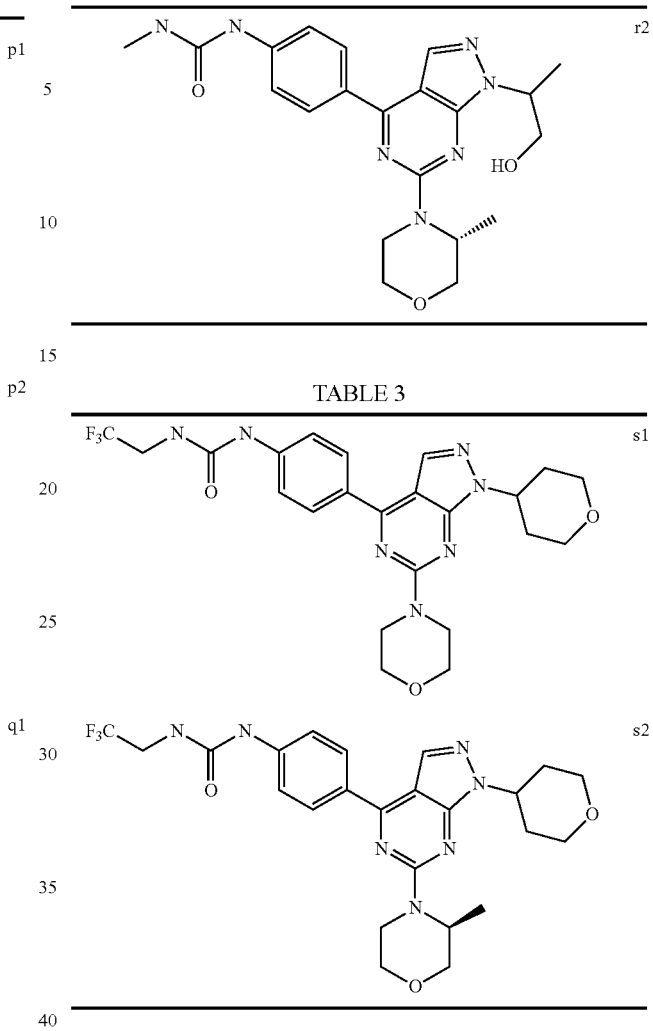

TABLE 3

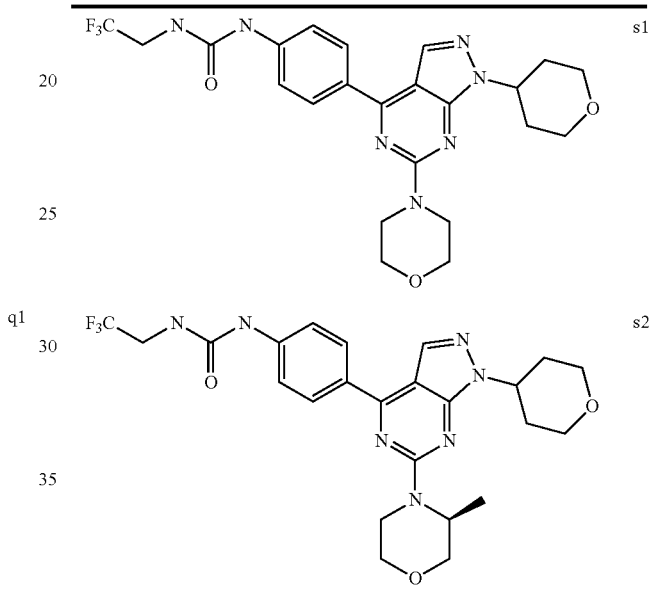

In one aspect, the compound is one of:
1-ethyl-3-[4-[1-(2-hydroxy-2-methyl-propyl)-6-morpholino-pyrazolo[3,4-d]pyrimidin-4-yl]phenyl]urea;
1-[4-[1-(2-hydroxy-2-methyl-propyl)-6-morpholino-pyrazolo[3,4-d]pyrimidin-4-yl]phenyl]-3-methyl-urea;
1-[4-(1-isopropyl-6-morpholino-pyrazolo[3,4-d]pyrimidin-4-yl)phenyl]-3-methyl-urea;
1-[4-(1-isopropyl-6-morpholino-pyrazolo[3,4-d]pyrimidin-4-yl)phenyl]-3-[4-(4-methylpiperazin-1-yl)phenyl]urea;
1-[4-(1-isopropyl-6-morpholino-pyrazolo[3,4-d]pyrimidin-4-yl)phenyl]-3-[4-(4-methylpiperazine-1-carbonyl)phenyl]urea;
methyl 4-[4-[4-(methylcarbamoylamino)phenyl]-6-morpholino-pyrazolo[3,4-d]pyrimidin-1-yl]piperidine-1-carboxylate;
1-methyl-3-[4-[1-[1-(4-methylpiperazine-1-carbonyl)-4-piperidyl]-6-morpholino-pyrazolo[3,4-d]pyrimidin-4-yl]phenyl]urea;
1-[4-[1-[1-[(2S)-2-aminopropanoyl]-4-piperidyl]-6-morpholino-pyrazolo[3,4-d]pyrimidin-4-yl]phenyl]-3-methyl-urea;
1-[4-[1-[1-(2-hydroxyacetyl)-4-piperidyl]-6-morpholino-pyrazolo[3,4-d]pyrimidin-4-yl]phenyl]-3-methyl-urea;
1-[4-[1-[1-[(2S)-2-hydroxypropanoyl]-4-piperidyl]-6-morpholino-pyrazolo[3,4-d]pyrimidin-4-yl]phenyl]-3-methylurea;

1-[4-[1-[1-(2-methoxyacetyl)-4-piperidyl]-6-morpholino-pyrazolo[3,4-d]pyrimidin-4-yl]phenyl]-3-methyl-urea;
1-methyl-3-[4-[1-(1-methylsulfonyl-4-piperidyl)-6-morpholino-pyrazolo[3,4-d]pyrimidin-4-yl]phenyl]urea;
1-methyl-3-[4-(6-morpholino-1-tetrahydropyran-4-yl-pyrazolo[3,4-d]pyrimidin-4-yl)phenyl]urea;
1-methyl-3-[4-[6-(8-Oxa-3-azabicyclo[3.2.1]octan-3-yl)-1-tetrahydropyran-4-yl-pyrazolo[3,4-d]pyrimidin-4-yl]phenyl]urea;
1-methyl-3-[4-[6-[(3S)-3-methylmorpholin-4-yl]-1-tetrahydropyran-4-yl-pyrazolo[3,4-d]pyrimidin-4-yl]phenyl]urea;
1-[4-[1-(2-hydroxy-2-methyl-propyl)-6-[(3S)-3-methylmorpholin-4-yl]pyrazolo[3,4-d]pyrimidin-4-yl]phenyl]-3-methyl-urea;
1-[4-[1-(2-hydroxy-2-methyl-propyl)-6-[(3R)-3-methylmorpholin-4-yl]pyrazolo[3,4-d]pyrimidin-4-yl]phenyl]-3-methyl-urea;
1-[4-[1-(2-hydroxyethyl)-6-[(3S)-3-methylmorpholin-4-yl]pyrazolo[3,4-d]pyrimidin-4-yl]phenyl]-3-methyl-urea;
1-[4-[1-(2-hydroxyethyl)-6-[(3R)-3-methylmorpholin-4-yl]pyrazolo[3,4-d]pyrimidin-4-yl]phenyl]-3-methyl-urea;
1-[4-[1-(2-hydroxy-1-methyl-ethyl)-6-[(3S)-3-methylmorpholin-4-yl]pyrazolo[3,4-d]pyrimidin-4-yl]phenyl]-3-methyl-urea;
1-[4-[1-(2-hydroxy-1-methyl-ethyl)-6-[(3R)-3-methylmorpholin-4-yl]pyrazolo[3,4-d]pyrimidin-4-yl]phenyl]-3-methyl-urea;
1-[4-(6-morpholino-1-tetrahydropyran-4-yl-pyrazolo[3,4-d]pyrimidin-4-yl)phenyl]-3-(2,2,2-trifluoroethyl)urea;
1-[4-[6-[(3S)-3-methylmorpholin-4-yl]-1-tetrahydropyran-4-yl-pyrazolo[3,4-d]pyrimidin-4-yl]phenyl]-3-(2,2,2-trifluoroethyl)urea.

The synthesis of compounds of the formulae herein can be readily effected by synthetic chemists of ordinary skill Relevant procedures and intermediates are disclosed, for instance, herein. Each of the patents, patent applications, and publications, whether in traditional journals or available only through the internet, referred to herein, is incorporated in its entirety by reference.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, $R^3$, $R^4$, R', X, etc.) or not. The suitability of a chemical group in a compound structure for use in synthesis of another compound structure is within the knowledge of one of ordinary skill in the art. Additional methods of synthesizing compounds of the formulae herein (e.g., Formula II) and their synthetic precursors, including those within routes not explicitly shown in schemes herein, are within the means of chemists of ordinary skill in the art. Methods for optimizing reaction conditions, if necessary minimizing competing by-products, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein (e.g., Formula II), or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in—Oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-Oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-Chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs; Elsevier: Amsterdam,* 1985; pp 1-92; Bundgaard, H.; Nielsen, N. M. *Journal of Medicinal Chemistry* 1987, 30, 451-454; Bundgaard, H. A *Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other chemotherapeutic agents for the treatment of the diseases and disorders discussed above.

Such agents are described in detail in the art. Preferably, the second therapeutic agent is an agent useful in the treatment or prevention of a disease or condition selected from cancer.

Even more preferably the second therapeutic agent co-formulated with a compound of this invention is an agent useful in the treatment of mTOR-mediated disease/disorders such as cancer, immune disorders, cardiovascular disease, ocular disease, viral infection, inflammation, metabolism/endocrine disorders and neurological disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Such diseases are well known in the art and are also disclosed herein.

In one aspect, the method of treating involves treatment of a disorder that is mediated by mTOR. In a preferred embodiment, the method of this invention is used to treat a subject suffering from or susceptible to a disease or condition such as discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity.

Examples of cancers which the present compounds can be used to treat include leukemia, brain tumors, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colonrectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

In one aspect, the method of treating involves treatment of a disorder that is mediated by the mTOR kinase.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method of modulating the activity of mTOR in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein (e.g., Formula II, III and IV) alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radio-labelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein (e.g., Formula II) or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

Example 1

1-ethyl-3-[4-[1-(2-hydroxy-2-methyl-propyl)-6-morpholino-pyrazolo[3,4-d]pyrimidin-4-yl]phenyl]urea

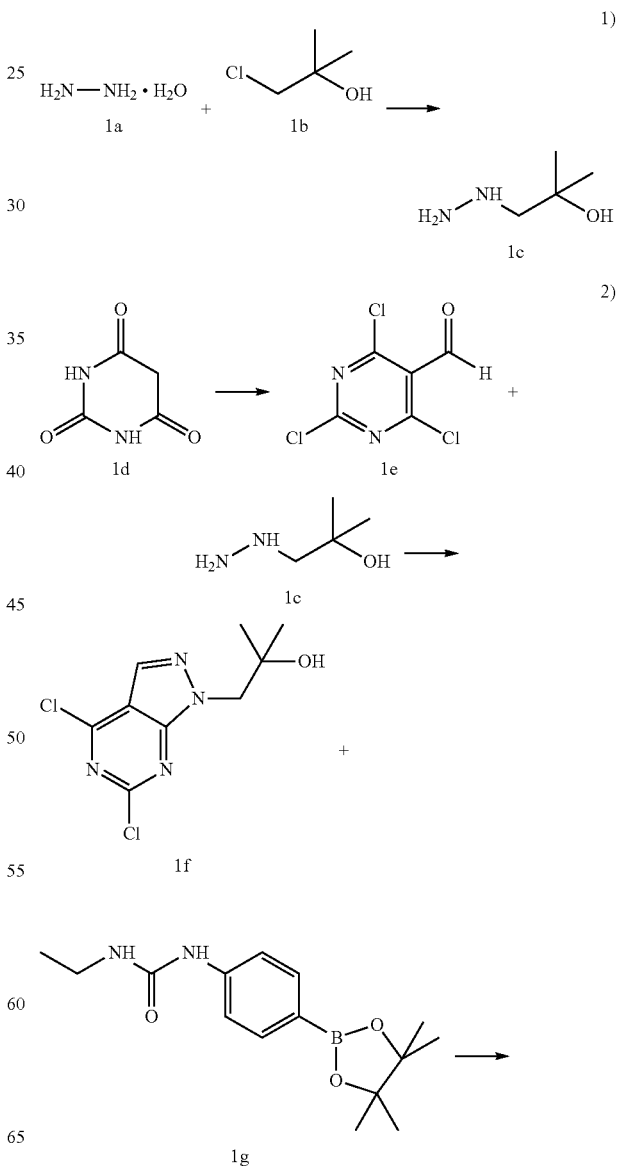

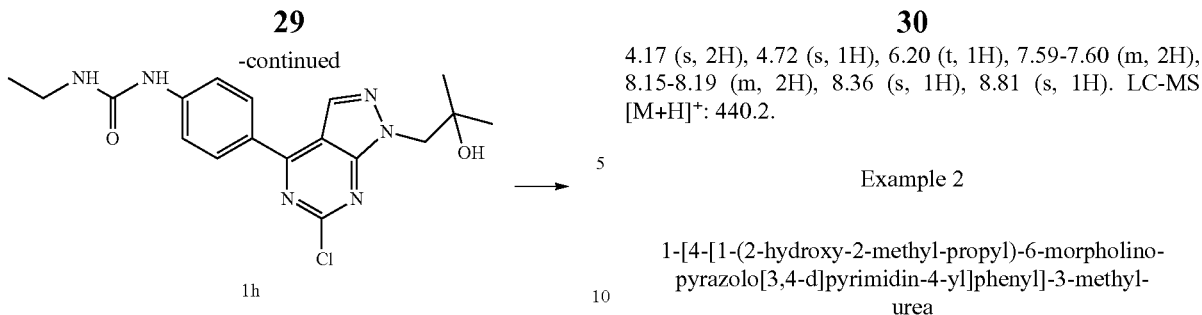

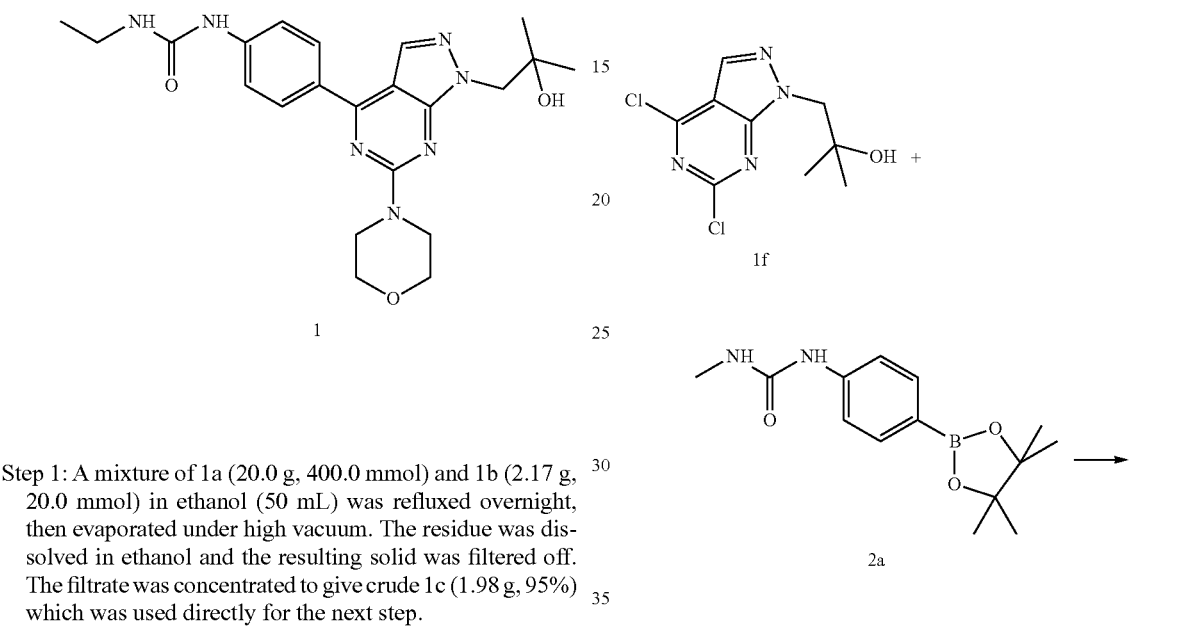

Step 1: A mixture of 1a (20.0 g, 400.0 mmol) and 1b (2.17 g, 20.0 mmol) in ethanol (50 mL) was refluxed overnight, then evaporated under high vacuum. The residue was dissolved in ethanol and the resulting solid was filtered off. The filtrate was concentrated to give crude 1c (1.98 g, 95%) which was used directly for the next step.

Step 2: DMF (9.5 g, 130 mmol) was added drop-wise to POCl₃ (47 mL) at 10° C. To this mixture, was slowly added 1d (10 g, 78.1 mmol) over a period of 20 min at −10° C. After the addition was complete, the resulting mixture was heated to reflux overnight, then evaporated. The residue was slowly added to water with stirring, then filtered and dried to give 1e (9.96 g, 60.4%).

Step 3: To a solution of 1e (2.45 g, 11.6 mmol) in EtOH (150 mL) was added dropwise a solution of 1c (1.21 g, 11.6 mmol) in EtOH (10 mL), followed by TEA (4.9 mL, 34.9 mmol) at −78° C. The resulting mixture was stirred at −78° C. for 30 min, then warmed to 0° C. for another 30 min. The mixture was adjusted to pH=5~6 with 3N HCl subsequently, then evaporated, The residue was purified by flash column (EA:PE=1:4) to provide 1f (1.84 g, 61%).

Step 4: To a solution of 1f (0.52 g, 2.0 mmol) and 1g (0.58 g, 2.0 mmol) in a mixture of acetonitrile (15 mL)/water (15 mL) was added Na₂CO₃ (0.46 g, 4.0 mmol) and Pd(Ph₃P)₄ (115 mg, 0.1 mmol). The mixture was degassed three times with N₂, then heated at 50° C. overnight. The solvent was evaporated and the residue purified by column chromatography (DCM: CH₃OH=20:1) to give 1 h (0.25 g, 32% yield).

Step 4: The mixture of 1h (74 mg, 0.19 mmol) in morpholine (2 mL) was heated at 80° C. for 2 h, then evaporated. The residue was triturated with ethanol and filtered to give 1 (64 mg, 77% yield). 1H-NMR (300 MHz, DMSO-d₆): δ=1.06 (t, 3H), 1.11 (s, 6H), 3.07-3.16 (m, 2H), 3.69 (t, 4H), 3.86 (t, 4H), 4.17 (s, 2H), 4.72 (s, 1H), 6.20 (t, 1H), 7.59-7.60 (m, 2H), 8.15-8.19 (m, 2H), 8.36 (s, 1H), 8.81 (s, 1H). LC-MS [M+H]⁺: 440.2.

Example 2

1-[4-[1-(2-hydroxy-2-methyl-propyl)-6-morpholino-pyrazolo[3,4-d]pyrimidin-4-yl]phenyl]-3-methyl-urea

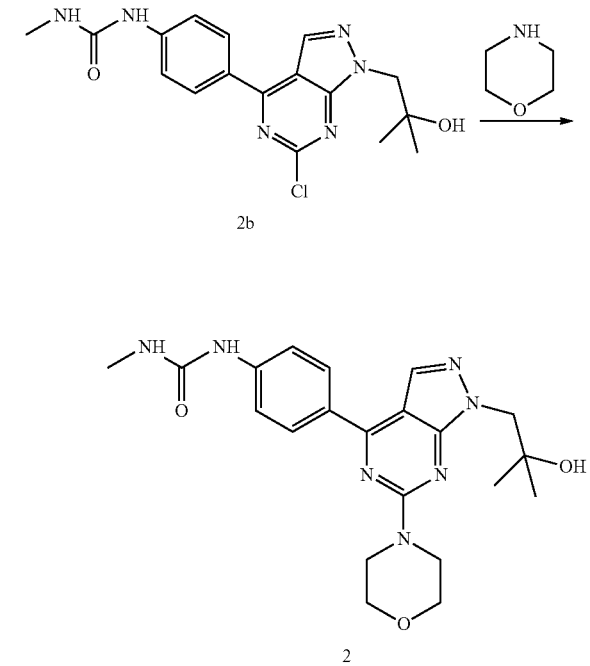

The procedure from 1f to 2 was similar to that of 1f to 1 which provided 2 (294 mg, 34.5% from 1f). 1H-NMR (300 MHz, DMSO-d6): δ=1.12 (s, 6H), 2.68 (d, 3H), 3.68-3.75 (m, 4H), 3.83-3.88 (m, 4H), 4.18 (s, 2H), 4.76 (s, 1H), 6.14 (q, 1H), 7.61 (d, 2H), 8.19 (d, 2H), 8.39 (s, 1H), 8.93 (s, 1H). LC-MS [M+H]$^+$: 426.3.
Example 3
1-[4-(1-isopropyl-6-morpholino-pyrazolo[3,4-d]pyrimidin-4-yl)phenyl]-3-methyl-urea
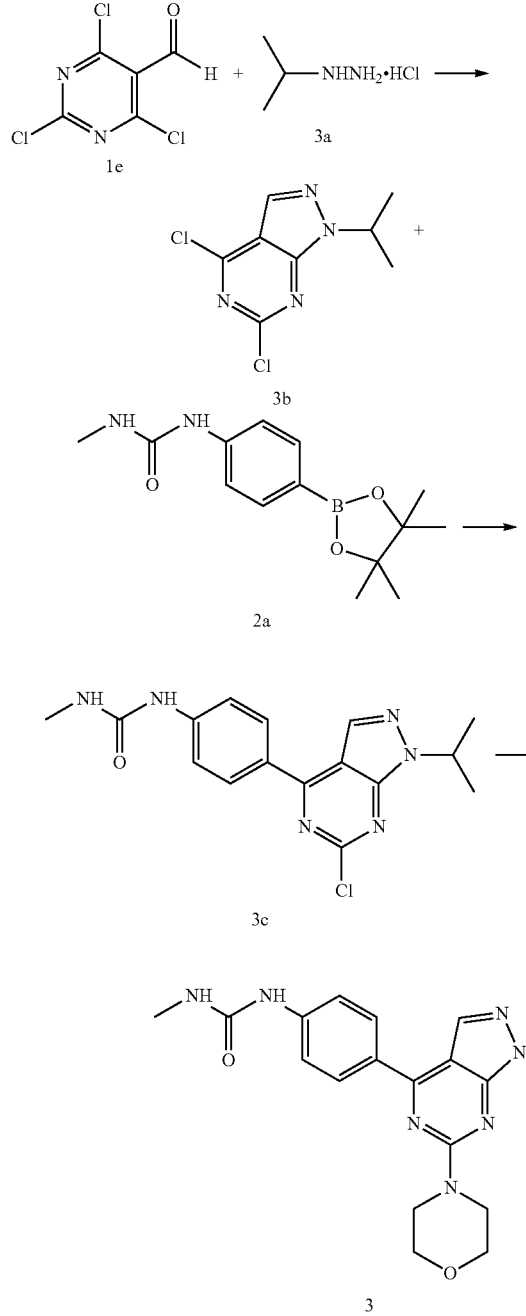
The procedure from 1e to 3 was similar to that of 1e to 1 which provided 3 (91 mg, 41% from 1e). 1H-NMR (300 MHz, DMSO-d$_6$): δ=1.42 (d, 6H), 2.64 (s, 3H), 3.69-3.84 (m, 8H), 4.90-4.99 (m, 1H), 6.14 (d, 1H), 7.58 (d, 2H), 8.14 (d, 2H), 8.33 (s, 1H). LC-MS [M+H]$^+$: 396.2.
Example 4
1-[4-(1-isopropyl-6-morpholino-pyrazolo[3,4-d]pyrimidin-4-yl)phenyl]-3-[4-(4-methylpiperazin-1-yl)phenyl]urea
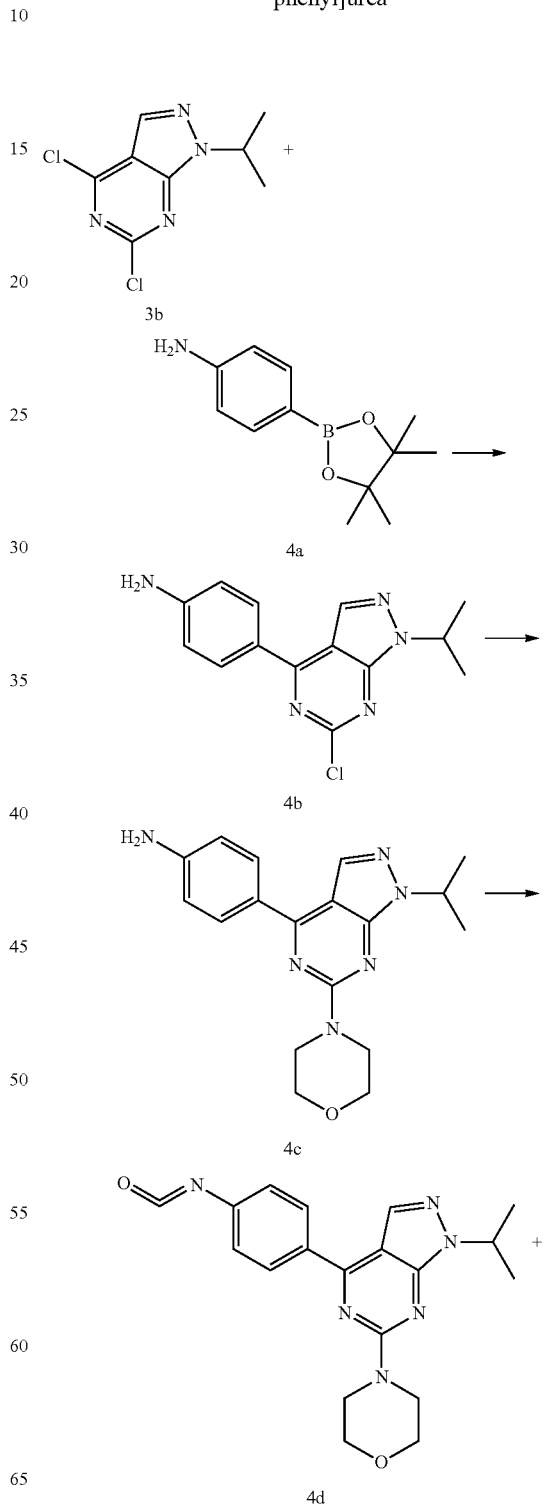

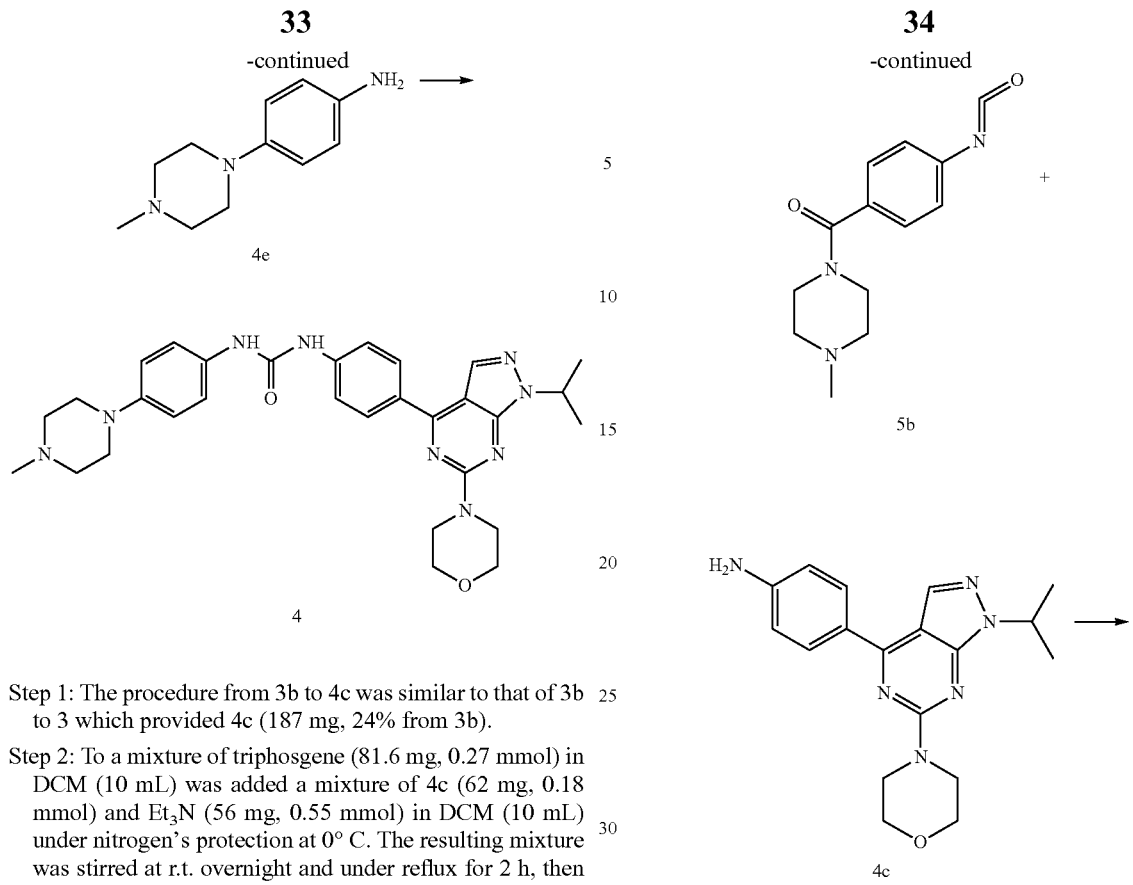

Step 1: The procedure from 3b to 4c was similar to that of 3b to 3 which provided 4c (187 mg, 24% from 3b).

Step 2: To a mixture of triphosgene (81.6 mg, 0.27 mmol) in DCM (10 mL) was added a mixture of 4c (62 mg, 0.18 mmol) and Et$_3$N (56 mg, 0.55 mmol) in DCM (10 mL) under nitrogen's protection at 0° C. The resulting mixture was stirred at r.t. overnight and under reflux for 2 h, then evaporated. The obtained residue was used directly for next step.

Step 3: To a mixture of 4d obtained from last step and 4e (37 mg, 0.19 mmol) in DCM (20 mL) was added Et$_3$N (37 mg, 0.37 mmol), the resulting mixture was heated under reflux for 2 h, cooled, and evaporated. The residue was triturated with methanol and filtered to provide 4 (56 mg, 55%).: $^1$H-NMR (300 MHz, DMSO-d$_6$): δ=1.43 (d, 6H), 2.20 (s, 3H), 2.43 (t, 4H), 3.04 (t, 4H), 3.70 (t, 4H), 3.86 (t, 4H), 4.91-5.01 (m, 1H), 6.86 (d, 2H), 7.28 (d, 2H), 7.62 (d, 2H), 8.18 (d, 2H), 8.36 (s, 1H), 8.50 (s, 1H), 8.96 (s, 1H). LC-MS [M+H]$^+$: 556.3.

Example 5

1-[4-(1-isopropyl-6-morpholino-pyrazolo[3,4-d]pyrimidin-4-yl)phenyl]-3-[4-(4-methylpiperazine-1-carbonyl)phenyl]urea

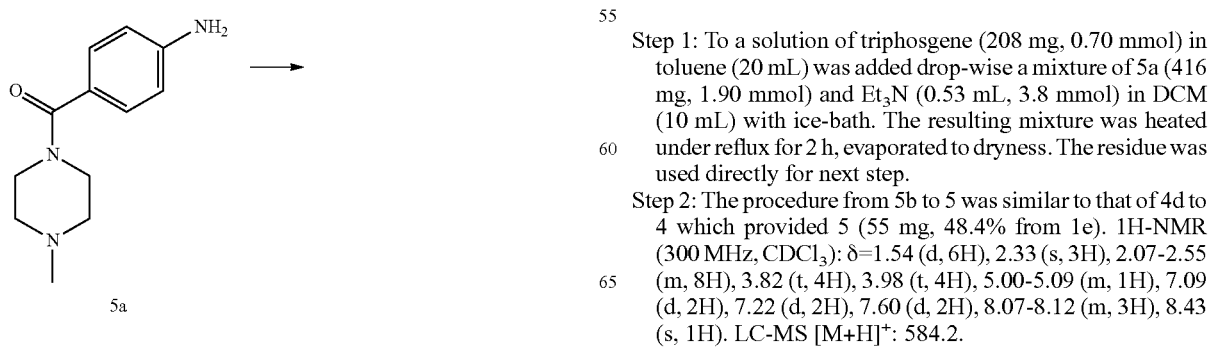

Step 1: To a solution of triphosgene (208 mg, 0.70 mmol) in toluene (20 mL) was added drop-wise a mixture of 5a (416 mg, 1.90 mmol) and Et$_3$N (0.53 mL, 3.8 mmol) in DCM (10 mL) with ice-bath. The resulting mixture was heated under reflux for 2 h, evaporated to dryness. The residue was used directly for next step.

Step 2: The procedure from 5b to 5 was similar to that of 4d to 4 which provided 5 (55 mg, 48.4% from 1e). 1H-NMR (300 MHz, CDCl$_3$): δ=1.54 (d, 6H), 2.33 (s, 3H), 2.07-2.55 (m, 8H), 3.82 (t, 4H), 3.98 (t, 4H), 5.00-5.09 (m, 1H), 7.09 (d, 2H), 7.22 (d, 2H), 7.60 (d, 2H), 8.07-8.12 (m, 3H), 8.43 (s, 1H). LC-MS [M+H]$^+$: 584.2.

Example 6 methyl 4-[4-[4-(methylcarbamoylamino)phenyl]-6-morpholino-pyrazolo[3,4-d]pyrimidin-1-yl]piperidine-1-carboxylate

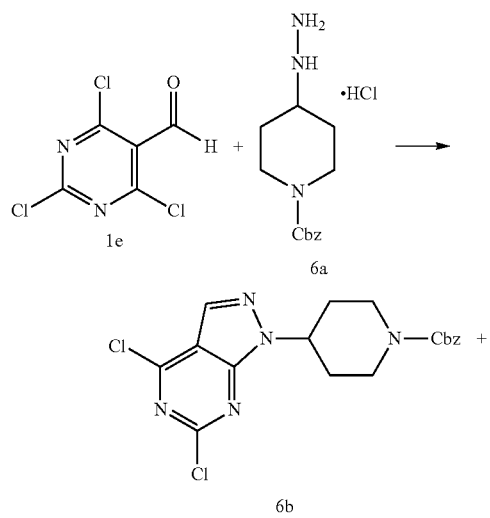

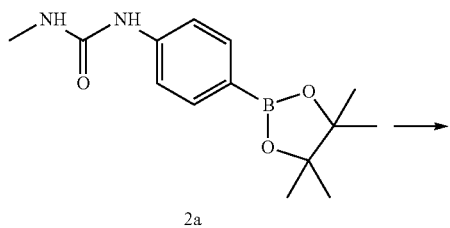

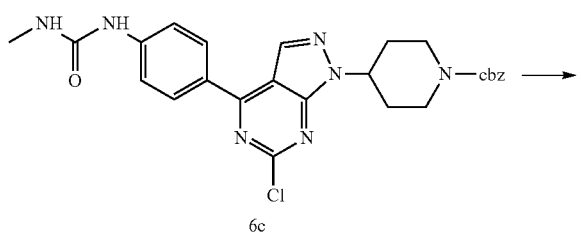

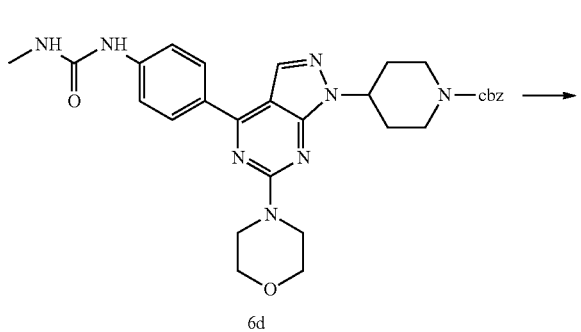

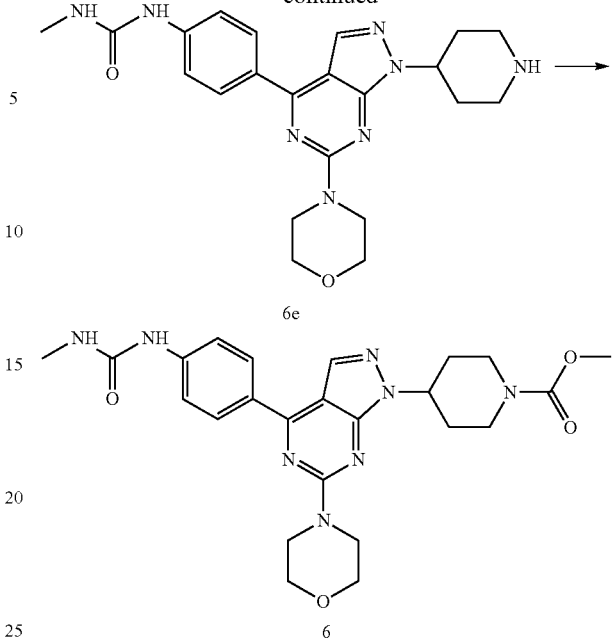

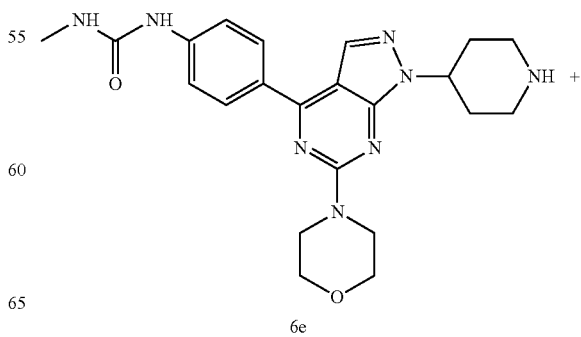

Step 1: The procedure from 1e to 6d was similar to that of 1e to 1 which provided 6d (860 mg, 41.8% from 1e).

Step 2: To a solution of 6d (860 mg, 1.51 mmol) in methanol (20 mL) was added 10% Pd/C (430 mg). The resulting mixture was hydrogenated at $H_2$ atmosphere at r.t. overnight. After the reaction was completed, the mixture was filtered and washed with methanol, dried to give 6e (627 mg, 95%).

Step 3: To a solution of 6e (38 mg, 0.87 mmol) and Et3N (26 mg, 0.26 mmol) in DMF (3 mL) was added methyl chlorooate (13 mg, 0.13 mmol) at 0° C., then the resulting mixture was warmed to r.t. for 1 h. After reaction was completed, the solvent was evaporated and the residue was triturated with methanol and filtered to provide 6 (86 mg, 86%). 1H-NMR (300 MHz, DMSO-$d_6$): δ=1.86-2.00 (m, 4H), 2.64 (d, 3H), 2.96-3.12 (m, 2H), 3.60 (s, 3H), 3.69 (t, 4H), 3.85 (t, 4H), 4.04-4.10 (m, 2H), 4.74-4.84 (m, 1H), 6.12 (q, 1H), 7.56 (d, 2H), 8.12 (d, 2H), 8.35 (s, 1H), 8.91 (s, 1H). LC-MS [M+H]$^+$: 495.2.

Example 7

1-methyl-3-[4-[1-[1-(4-methylpiperazine-1-carbonyl)-4-piperidyl]-6-morpholino-pyrazolo[3,4-d]pyrimidin-4-yl]phenyl]urea

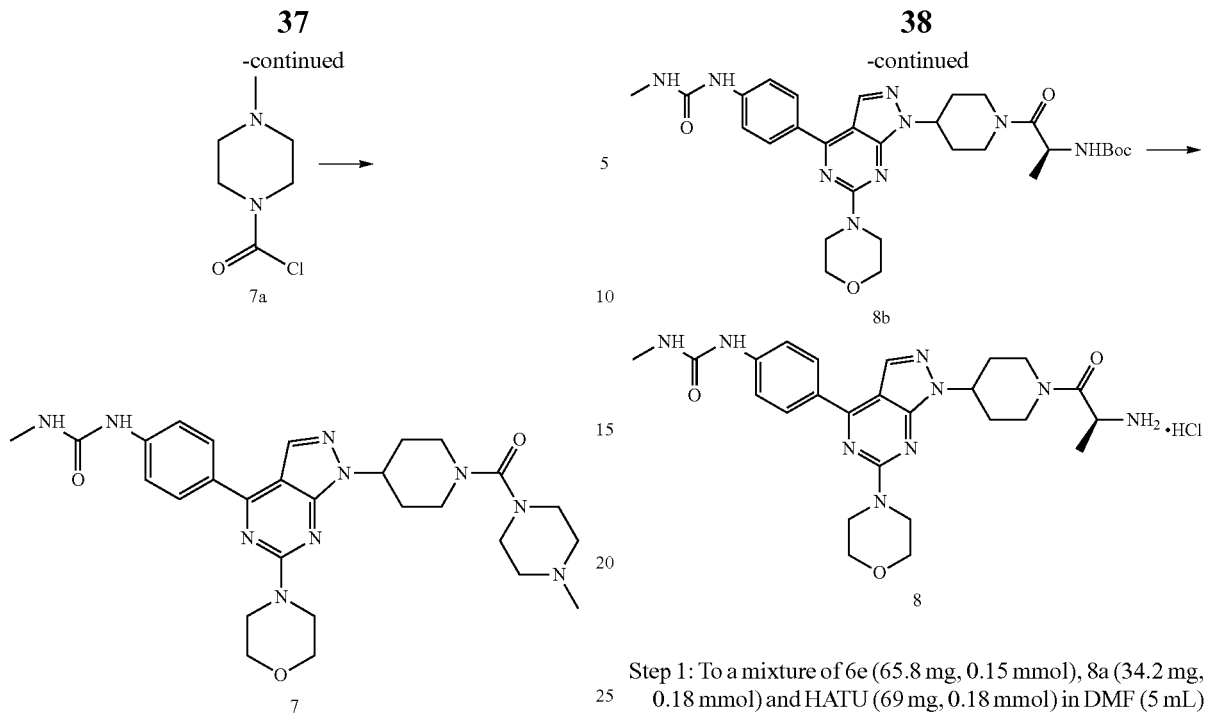

The procedure from 6e to 7 was similar to that of 6e to 6 which provided 7 (80 mg, 95.2%). 1H-NMR (300 MHz, DMSO-d$_6$): δ=1.82-1.93 (m, 2H), 2.03-2.17 (m, 2H), 2.65 (d, 3H), 2.76 (s, 3H), 3.00-3.40 (m, 8H), 3.60-3.89 (m, 12H), 4.76-4.86 (m, 1H), 6.23 (q, 1H), 7.59 (d, 2H), 8.15 (d, 2H), 8.38 (s, 1H), 9.10 (s, 1H), 10.47 (s, 1H). LC-MS [M+H]$^+$: 563.3.

Example 8

1-[4-[1-[1-[(2S)-2-aminopropanoyl]-4-piperidyl]-6-morpholino-pyrazolo[3,4-d]pyrimidin-4-yl]phenyl]-3-methyl-urea

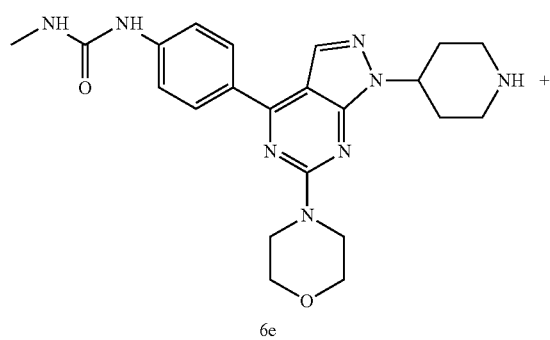

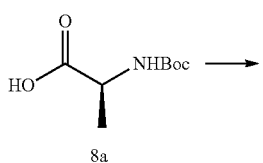

Step 1: To a mixture of 6e (65.8 mg, 0.15 mmol), 8a (34.2 mg, 0.18 mmol) and HATU (69 mg, 0.18 mmol) in DMF (5 mL) was added DIEA (39.0 mg, 0.30 mmol), the resulting mixture was stirred at r.t. for 2 h, evaporated and the residue was triturated with methanol and filtered to give 8b (70 mg, 76%).

Step 2: To a solution of 8b (70 mg, 0.12 mmol) in DCM (5 mL) was added a solution of 6NHCl/Et2O (5 mL). The mixture was stirred at r.t. overnight, then filtered to afford 8 (71 mg, about 100%). 1H-NMR (300 MHz, DMSO-d$_6$): δ=1.32-1.38 (m, 3H), 1.90-2.07 (m, 4H), 2.66 (s, 3H), 2.90-3.03 (m, 1H), 3.32-3.40 (m, 1H), 3.72 (t, 4H), 3.88 (t, 4H), 3.99 (brs, 2H), 4.38-4.53 (m, 2H), 4.86-4.98 (m, 1H), 7.60 (d, 2H), 8.15-8.21 (m, 5H), 8.39 (s, 1H), 9.32 (s, 1H). LC-MS [M+H]$^+$: 508.3.

Example 9

1-[4-[1-[1-(2-hydroxyacetyl)-4-piperidyl]-6-morpholino-pyrazolo[3,4-d]pyrimidin-4-yl]phenyl]-3-methyl-urea

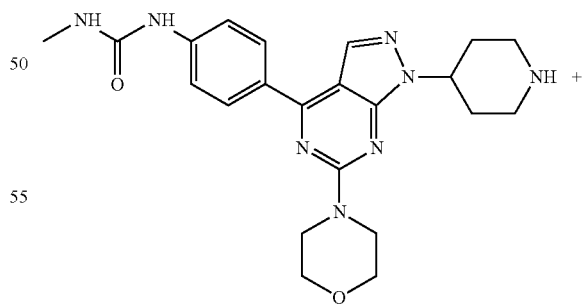

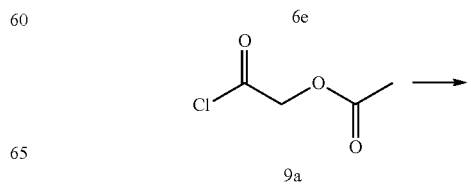

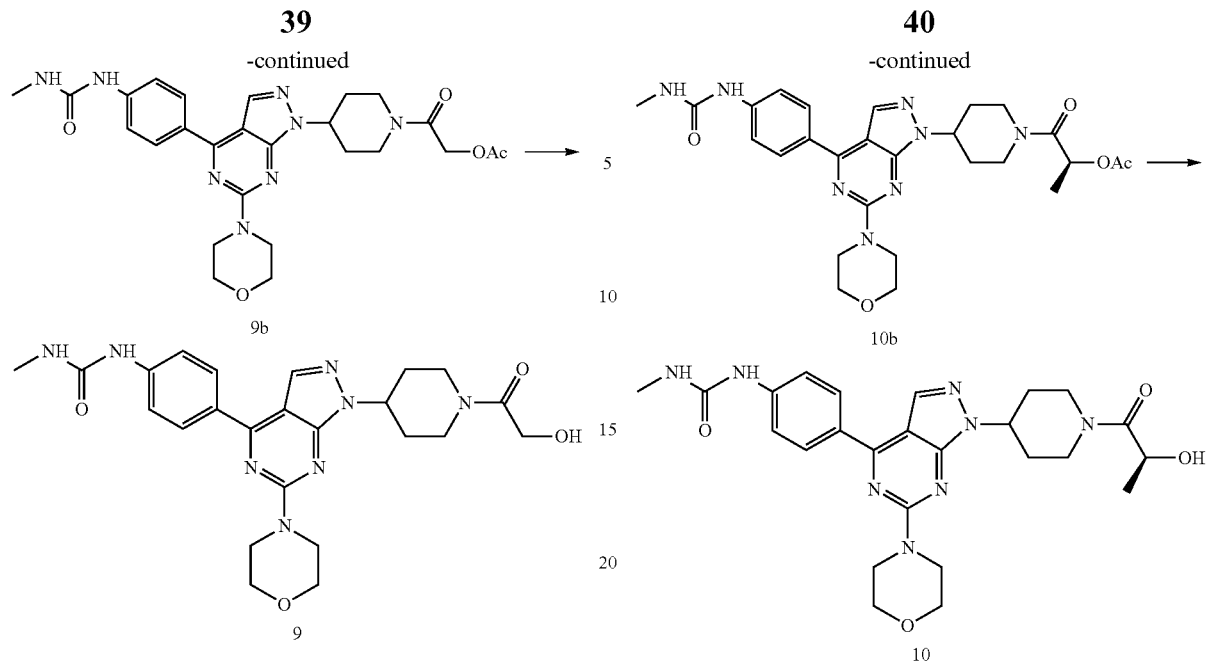

Step 1: The procedure from 6e to 9b was similar to that of 6e to 6 which provided crude 9b (without purification and used for the next step directly).

Step 2: To a solution of crude 9b obtained from last step in methanol (20 mL) was added aq. 1N NaOH (2.2 mL). Then the resulting mixture was stirred at r.t. overnight and evaporated. The residue was washed with water and methanol to give 9 (251 mg, 70% form 6e). 1H-NMR (300 MHz, DMSO-$d_6$): δ=1.91-2.08 (m, 4H), 2.65 (d, 3H), 2.85-2.90 (m, 2H), 3.15-3.21 (m, 1H), 3.66-3.87 (m, 9H), 4.10-4.16 (dd, 2H), 4.42-4.47 (m, 1H), 4.58 (t, 1H), 4.83-4.89 (m, 1H), 6.14 (q, 1H), 7.59 (d, 2H), 8.15 (d, 2H), 8.37 (s, 1H), 8.92 (s, 1H). LC-MS [M+H]$^+$: 495.2.

Example 10

1-[4-[1-[1-[(2S)-2-hydroxypropanoyl]-4-piperidyl]-6-morpholino-pyrazolo[3,4-d]pyrimidin-4-yl]phenyl]-3-methylurea Step 1: The procedure from 6e to 10b was similar to that of 6e to 6 which provided crude 10b (without purification and used directly for the next step).

Step 2: The procedure from 10b to 10 was similar to that of 9b to 9 which provided 10 (206 mg, 57%). 1H-NMR (300 MHz, DMSO-$d_6$): δ=1.22 (t, 3H), 1.89-2.10 (m, 4H), 2.66 (d, 3H), 2.84-2.88 (m, 1H), 3.24-3.32 (m, 1H), 3.71-3.88 (m, 8H), 4.12-4.18 (m, 1H), 4.44-4.51 (m, 2H), 4.85-4.98 (m, 2H), 6.15 (q, 1H), 7.61 (d, 2H), 8.17 (d, 2H), 8.39 (s, 1H), 8.95 (s, 1H). LC-MS [M+H]$^+$: 509.3.

Example 11

1-[4-[1-[1-(2-methoxyacetyl)-4-piperidyl]-6-morpholino-pyrazolo[3,4-d]pyrimidin-4-yl]phenyl]-3-methyl-urea

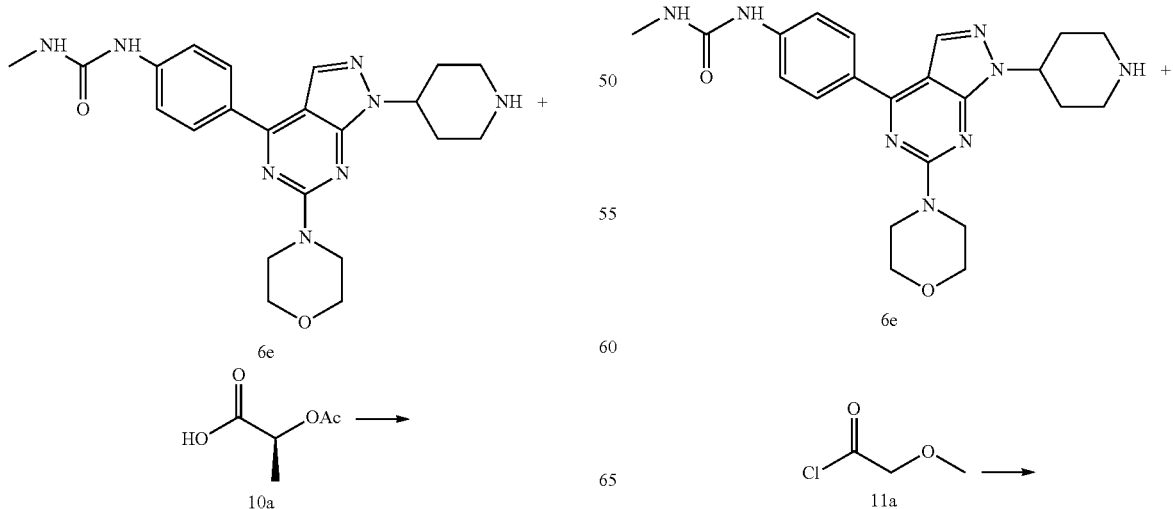

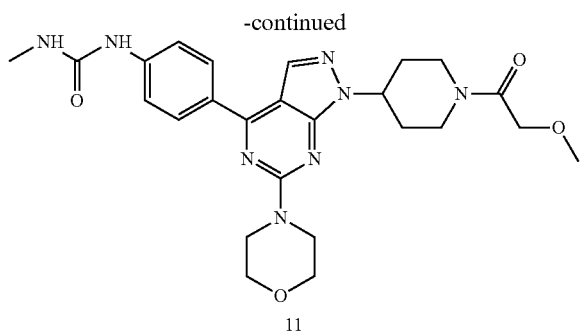

The procedure from 6e to 11 was similar to that of 6e to 6 which provided 11 (263 mg, 45%). 1H-NMR (300 MHz, DMSO-d$_6$): δ=1.92-2.12 (m, 4H), 2.67 (d, 3H), 2.83-2.88 (m, 1H), 3.24-3.28 (m, 2H), 3.31 (s, 3H), 3.70-3.94 (m, 9H), 4.13 (q, 2H), 4.43-4.48 (m, 1H), 4.85-4.89 (m, 1H), 6.13 (q, 1H), 7.61 (d, 2H), 8.17 (d, 2H), 8.38 (s, 1H), 8.92 (s, 1H). LC-MS [M+H]$^+$: 509.3.

Example 12

1-methyl-3-[4-[1-(1-methylsulfonyl-4-piperidyl)-6-morpholino-pyrazolo[3,4-d]pyrimidin-4-yl]phenyl]urea

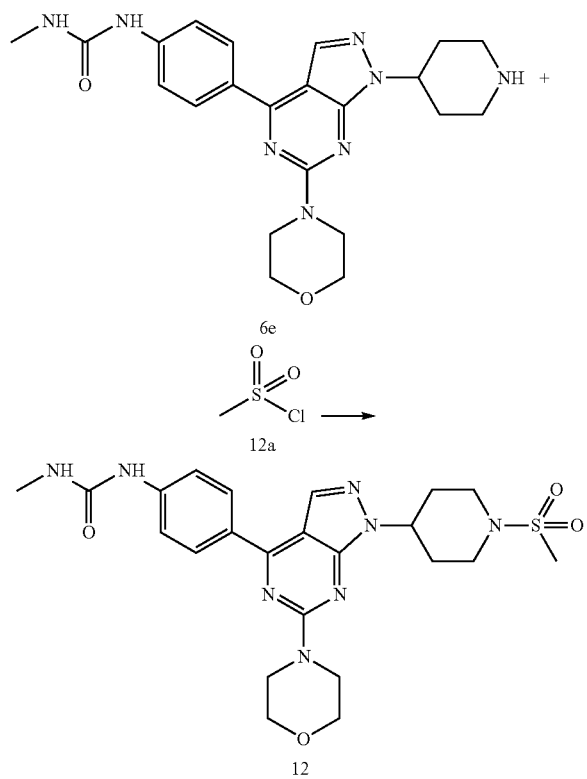

The procedure from 6e to 12 was similar to that of 6e to 6 which provided 12 (315 mg, 59%). 1H-NMR (300 MHz, DMSO-d$_6$): δ=1.98-2.03 (m, 2H), 2.10-2.18 (m, 2H), 2.66 (d, 3H), 2.94 (s, 3H), 2.96-3.07 (m, 2H), 3.66-3.74 (m, 6H), 3.84-3.91 (m, 4H), 4.73-4.76 (m, 1H), 6.15 (q, 1H), 7.61 (d, 2H), 8.18 (d, 2H), 8.40 (s, 1H), 8.93 (s, 1H). LC-MS [M+H]$^+$: 515.2.

Example 13

1-methyl-3-[4-(6-morpholino-1-tetrahydropyran-4-yl-pyrazolo[3,4-d]pyrimidin-4-yl)phenyl]urea

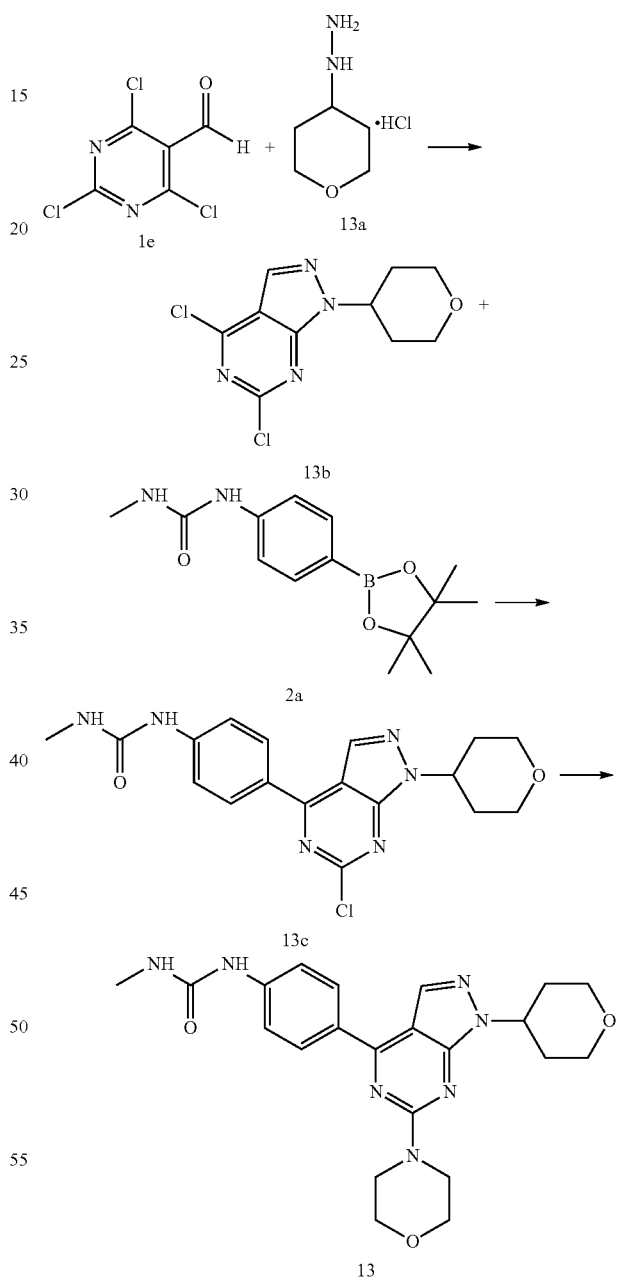

The procedure from 1e to 13 was similar to that of 1e to 1 which provided 13 (860 mg, 41.8% from 1e). 1H-NMR (300 MHz, DMSO-d$_6$): δ=1.82-1.87 (m, 2H), 2.10-2.20 (m, 2H), 2.65 (d, 3H), 3.53 (t, 2H), 3.71 (t, 4H), 3.87 (t, 4H), 3.97-4.02 (m, 2H), 4.71-4.87 (m, 1H), 6.13 (q, 1H), 7.59 (d, 2H), 8.15 (d, 2H), 8.38 (s, 1H), 8.93 (s, 1H). LC-MS [M+H]$^+$: 438.3.

Example 14

1-methyl-3-[4-[6-(8-oxa-3-azabicyclo[3.2.1]octan-3-yl)-1-tetrahydropyran-4-yl-pyrazolo[3,4-d]pyrimidin-4-yl]phenyl]urea

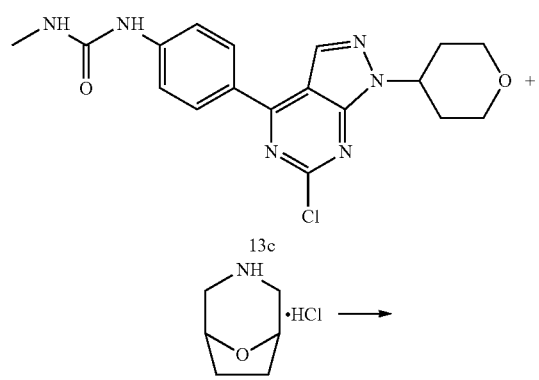
13c

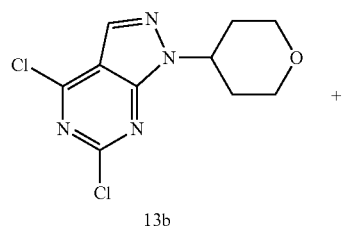
14a

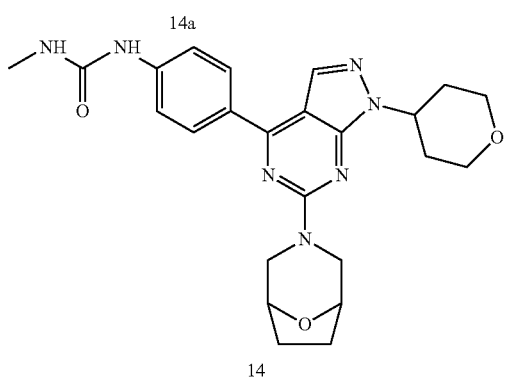
14

Step 1: To a solution of 13c (491 mg, 1.24 mmol) in DMF (15 mL) was added 14a (219 mg, 1.45 mmol), followed by Cs$_2$CO$_3$ (809 mg, 2.48 mmol). The resulting mixture was heated at 80° C. for 2 days, then evaporated under reduced pressure. The residue was washed with water and methanol to give 14 (410 mg, 71%). 1H-NMR (300 MHz, DMSO-d$_6$): δ=1.66-1.81 (m, 6H), 2.10-2.24 (m, 2H), 2.67 (d, 3H), 3.15-3.19 (m, 2H), 3.50-3.58 (m, 2H), 3.97-4.02 (m, 2H), 4.39-4.46 (m, 4H), 4.76-4.84 (m, 1H), 6.13 (q, 1H), 7.61 (d, 2H), 8.15 (d, 2H), 8.37 (s, 1H), 8.93 (s, 1H). LC-MS [M+H]$^+$: 464.2.

Example 15

1-methyl-3-[4-[6-[(3S)-3-methylmorpholin-4-yl]-1-tetrahydropyran-4-yl-pyrazolo[3,4-d]pyrimidin-4-yl]phenyl]urea

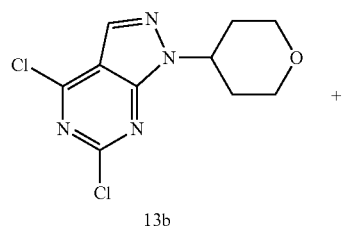
13b

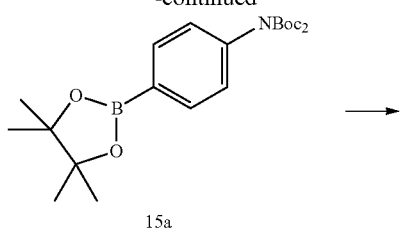
15a

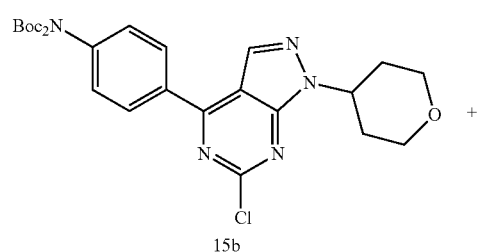
15b

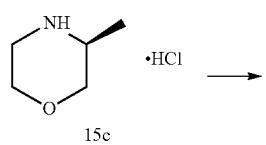
15c

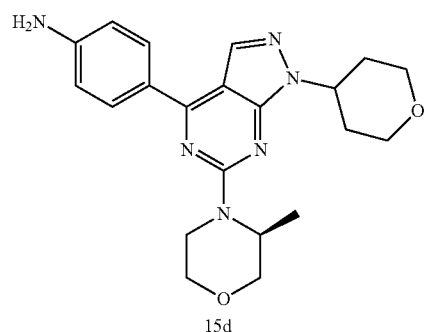
15d

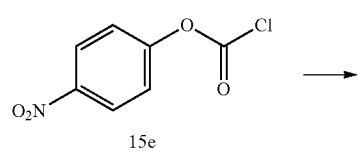
15e

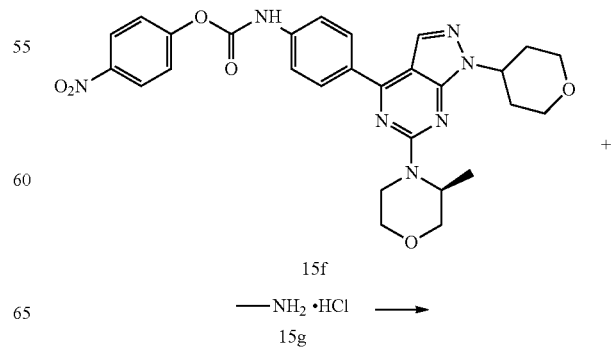
15f

—NH$_2$ •HCl
15g

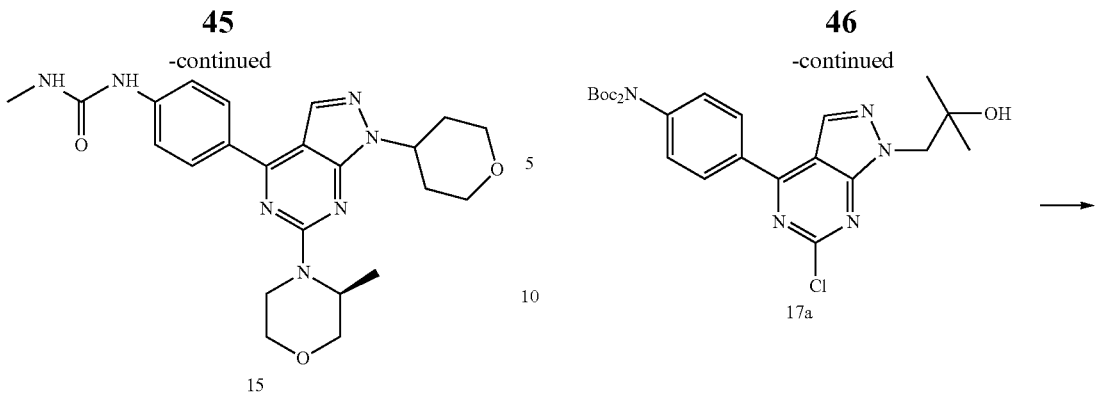

Step 1: The procedure from 13b to 15b was similar to that of 1f to 1h which provided 15b (1.55 g, 45%).

Step 2: A mixture of 15b (1.55 g, 3.6 mmol), 15c (0.64 g, 4.7 mmol) and Cs$_2$CO$_3$ (809 mg, 2.48 mmol) in NMP (20 mL) was heated at 150° C. overnight in a sealed-tube, then warmed to 160° C. and stirred for another 4 h. The solvent was evaporated in reduced pressure and the residue was purified by flash column to give 15d (743 mg, 52%).

Step 3: To a solution of 15e (220 mg, 1.10 mmol) in DMF (40 mL) was added pyridine (100 mg, 1.24 mmol) and 15d (410 mg, 1.04 mmol) at 0° C. The resulting mixture was stirred at r.t. overnight, then added to a solution of 15 g (210 mg, 3.11 mmol) and DIEA (375 mg, 2.91 mmol) in DMF (30 mL) at 0° C. After being stirred at r.t. for another 24 h, the solvent was evaporated. The residue was purified by flash column to give 15 (295 mg, 62%). 1H-NMR (300 MHz, DMSO-d$_6$): δ=1.23 (d, 3H), 1.81-1.87 (m, 2H), 2.12-2.18 (m, 2H), 2.65 (d, 3H), 3.22-3.31 (m, 1H), 3.42-3.77 (m, 6H), 3.92-4.00 (m, 3H), 4.45 (d, 1H), 4.77-4.85 (m, 2H), 6.16 (q, 1H), 7.60 (d, 2H), 8.14 (d, 2H), 8.35 (s, 1H), 8.94 (s, 1H). LC-MS [M+H]$^+$: 452.2.

Example 16

N-{4-[6-((3S)-3-methylmorpholin-4-yl)-1-(2-hydroxy-2-methylpropyl)pyrazolo[4,5-e]pyrimidin-4-yl]phenyl}(methylamino)carboxamide

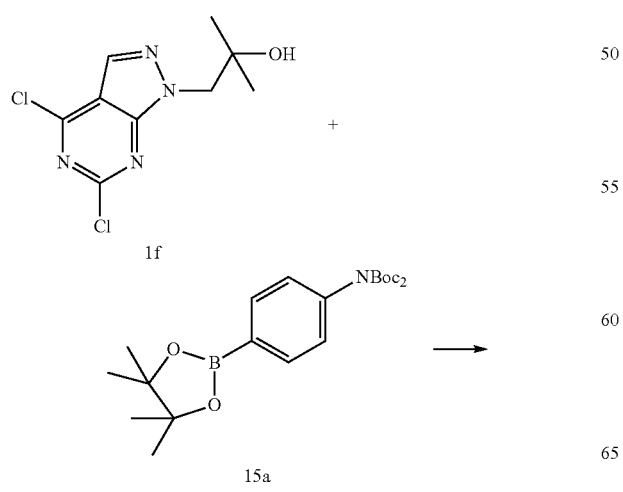

The procedure from 1f to 17 was similar to that of 13b to 15 which provided 17 (1.01 g, 26% from 1f). δ=1.12 (d, 6H), 1.23 (d, 3H), 2.67 (d, 3H), 3.18-3.28 (m, 1H), 3.44-3.52 (m, 1H), 3.61-3.66 (m, 1H), 3.93-3.98 (m, 1H), 4.12-4.25 (m, 2H), 4.46-4.51 (m, 1H), 4.77 (s, 1H), 4.78-4.84 (m, 1H), 6.14 (q, 1H), 7.61 (d, 2H), 8.17 (d, 2H), 8.37 (d, 1H), 8.92 (s, 1H). LC-MS [M+H]$^+$: 440.2

Example 17

N-{4-[6-((3R)-3-methylmorpholin-4-yl)-1-(2-hydroxy-2-methylpropyl)pyrazolo[4,5-e]pyrimidin-4-yl]phenyl}(methylamino)carboxamide

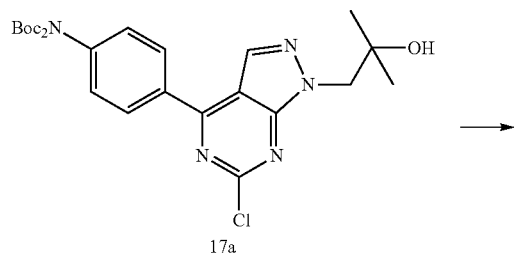
17a

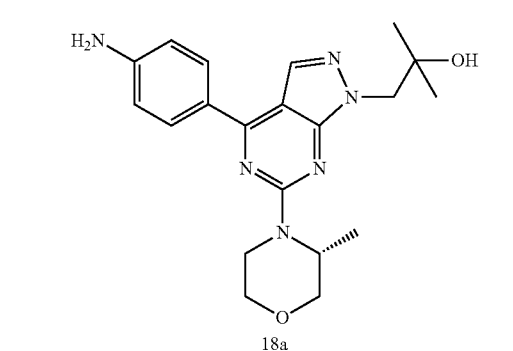
18a

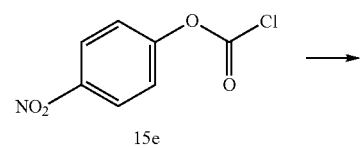
15e

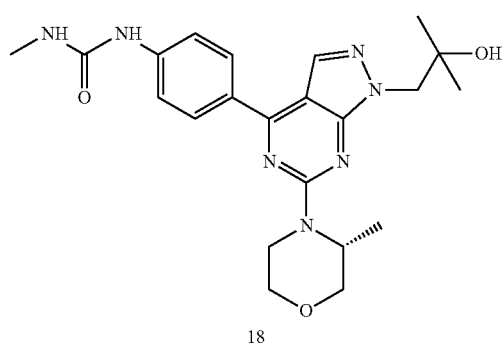
18

The procedure from 17a to 18 was similar to that of 17a to 17 which provided 18 (750 mg, 21% from 17a). 1H-NMR (300 MHz, DMSO-$d_6$): δ=1.12 (d, 6H), 1.23 (d, 3H), 2.67 (d, 3H), 3.18-3.28 (m, 1H), 3.44-3.52 (m, 1H), 3.61-3.66 (m, 1H), 3.93-3.98 (m, 1H), 4.12-4.25 (m, 2H), 4.46-4.51 (m, 1H), 4.77 (s, 1H), 4.78-4.84 (m, 1H), 6.14 (q, 1H), 7.61 (d, 2H), 8.17 (d, 2H), 8.37 (d, 1H), 8.92 (s, 1H). LC-MS [M+H]$^+$: 440.2

Example 18

N-{4-[1-(2H-3,4,5,6-tetrahydropyran-4-yl)-6-((3R)-3-methylmorpholin-4-yl)pyrazolo[4,5-e]pyrimidin-4-yl]phenyl}(methylamino)carboxamide

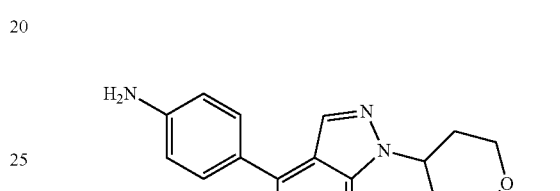
15b

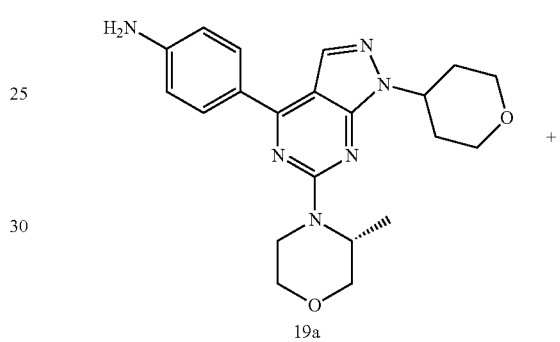
19a

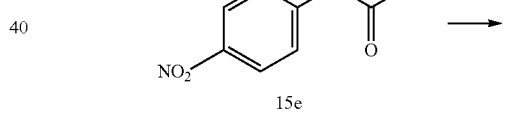
15e

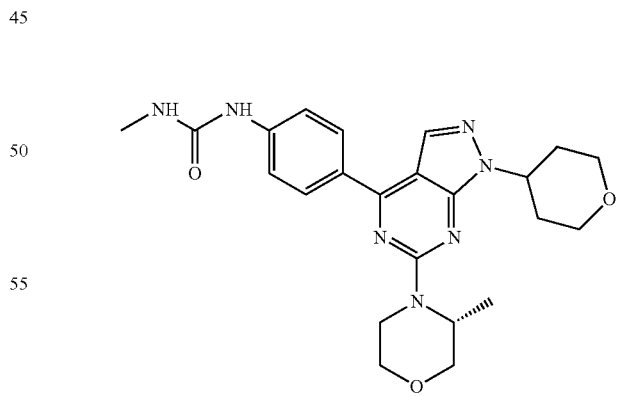
19

The procedure from 15b to 19 was similar to that of 15b to 15 which provided 19 (1.07 g, 32% from 15b). 1H-NMR (300 MHz, DMSO-$d_6$): δ=1.26 (d, 3H), 1.84-1.89 (m, 2H), 2.12-2.24 (m, 2H), 2.67 (d, 3H), 3.22-3.30 (m, 1H), 3.44-3.80 (m, 5H), 3.95-4.02 (m, 3H), 4.45-4.50 (m, 1H), 4.77-4.89 (m, 2H), 6.13 (q, 1H), 7.61 (d, 2H), 8.16 (d, 2H), 8.36 (d, 1H), 8.89 (s, 1H). LC-MS [M+H]+: 452.2

Example 19 ethyl 4-(4-{4-[(methylamino)carbonylamino]phenyl}-6-morpholin-4-yl pyrazolo[5,4-d]pyrimidinyl)cyclohexanecarboxylate

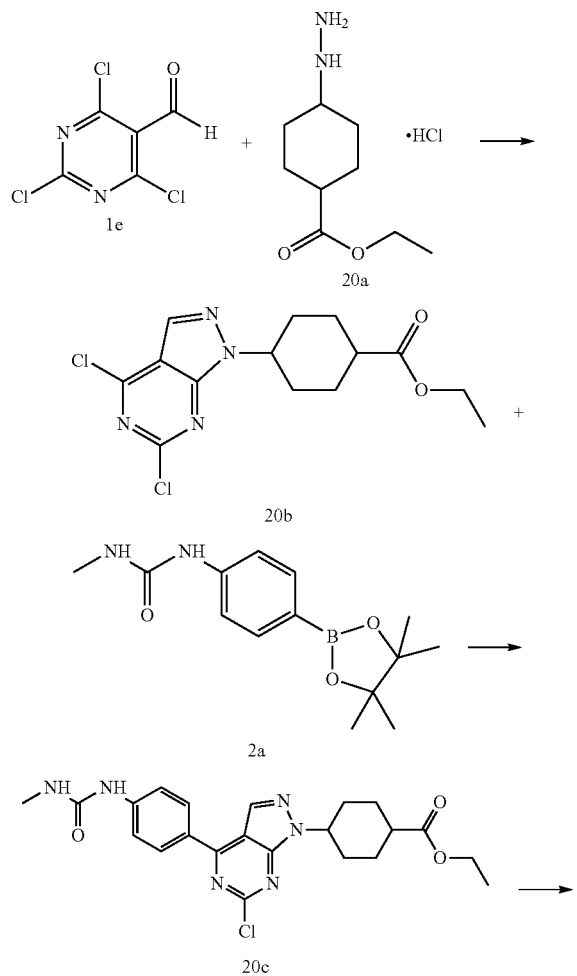

The procedure from 1e to 20 was similar to that of 1e to 1 which provided 20 (260 mg, 5.7% from 1e). 1H-NMR (300 MHz, DMSO-d$_6$): δ=1.18-1.25 (m, 3H), 1.61-2.19 (m, 8H), 2.67 (d, 3H), 2.70-2.73 (m, 1H), 3.71-3.73 (m, 4H), 3.85-3.87 (m, 4H), 4.05-4.17 (m, 2H), 4.58-4.63 (m, 1H), 6.13 (q, 1H), 7.61 (d, 2H), 8.16 (dd, 2H), 8.34 (d, 1H), 8.90 (s, 1H). LC-MS [M+H]+: 508.2

Example 20

N-(4-{1-[4-(hydroxymethyl)cyclohexyl]-6-morpholin-4-ylpyrazolo[4,5-e]pyrimidin-4-yl}phenyl)(methylamino)carboxamide

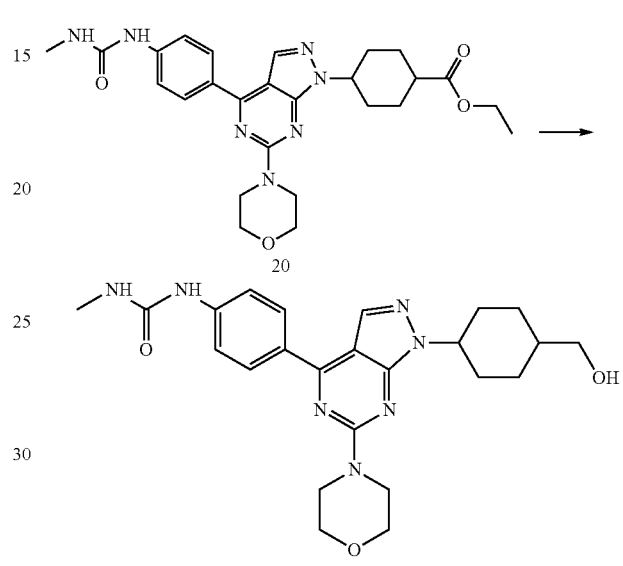

To a mixture of 20 (100 mg, 0.20 mol) in anhydrous THF (3 mL) was added LiAlH4 (15 mg, 0.39 mol) at 0° C. After being stirred at r.t. for 1.5 h, the mixture was quenched with methanol and filtered. The filtrate was concentrated and triturated with methanol to afford 21 (28 mg, 30%). 1H-NMR (300 MHz, DMSO-d6): δ=1.13-2.27 (m, 9H), 2.67 (d, 3H), 3.29 (t, 1H), 3.46 (t, 1H), 3.68-3.73 (m, 4H), 3.85-3.87 (m, 4H), 4.47 (q, 1H), 4.47-4.64 (m, 1H), 6.13 (q, 1H), 7.61 (d, 2H), 8.17 (d, 2H), 8.34 (s, 1H), 8.90 (s, 1H). LC-MS [M+H]+: 466.2

Example 21

4-(4-{4-[(methylamino)carbonylamino]phenyl}-6-morpholin-4-yl pyrazolo[5,4-d]pyrimidinyl)cyclohexanecarboxylic acid

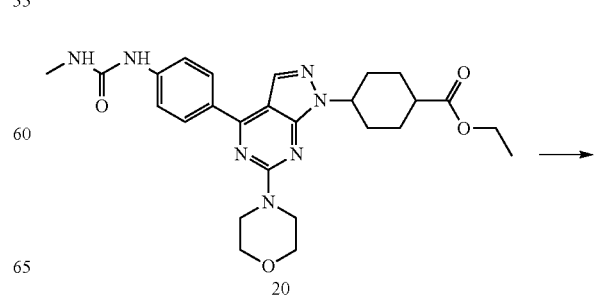

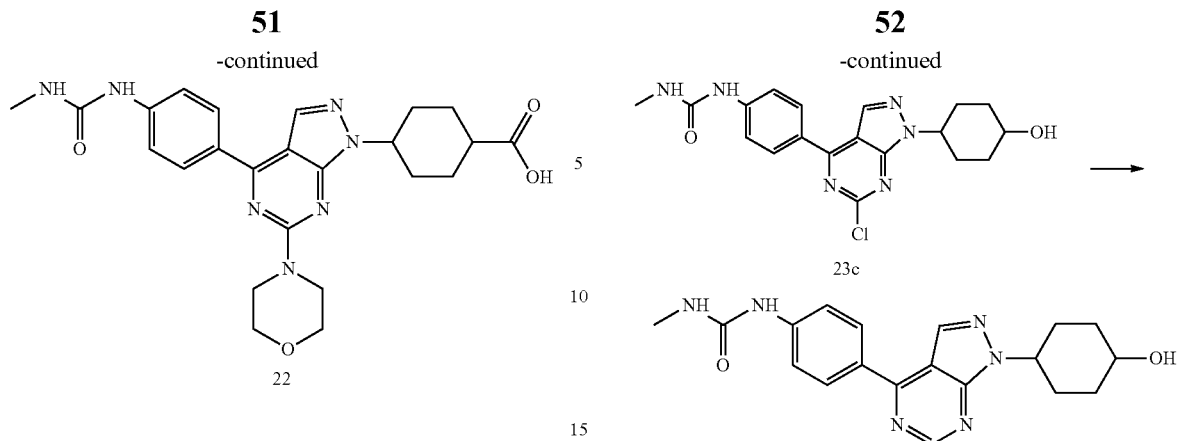

To a mixture of 20 (100 mg, 0.20 mol) in THF (4 mL) was added 1N NaOH (0.4 mL). After stirred at 60° C. for 2 h, the solvent was evaporated and the residue was acidified to pH=5-6 with 1N HCl, extracted with DCM (10 mL*3), dried over MgSO$_4$, concentrated and the residue was retreated with methanol, filtered to afford 22 (66 mg, 69%). 1H-NMR (300 MHz, DMSO-d$_6$): δ=1.54-2.31 (m, 9H), 2.67 (d, 3H), 3.71-3.73 (m, 4H), 3.85-3.88 (m, 4H), 4.56-4.62 (m, 1H), 6.20 (q, 1H), 7.61 (d, 2H), 8.16 (d, 2H), 8.34 (s, 1H), 8.97 (s, 1H), 12.19 (s, 1H). LC-MS [M+H]$^+$: 480.2.

Example 22

N-{4-[1-(4-hydroxycyclohexyl)-6-morpholin-4-ylpyrazolo[4,5-e]pyrimidin-4-yl]phenyl}(methylamino)carboxamide The procedure from 1e to 23 was similar to that of 1e to 1 which provided 23 (435 mg, 33% from 1e). 1H-NMR (300 MHz, DMSO-d$_6$): δ=1.32-2.37 (m, 8H), 2.66 (d, 3H), 3.48-3.55 (m, 1H), 3.71-3.73 (m, 4H), 3.82-3.87 (m, 4H), 4.50-4.58 (m, 1H), 4.67 (d, 1H), 6.13 (q, 1H), 7.61 (d, 2H), 8.16 (d, 2H), 8.34 (s, 1H), 8.91 (s, 1H). LC-MS [M+H]$^+$: 452.2.

Example 23

4-[6-((3S)-3-methylmorpholin-4-yl)-4-(4-aminophenyl)pyrazolo[5,4-d]pyrimidinyl]cyclohexan-1-Ol

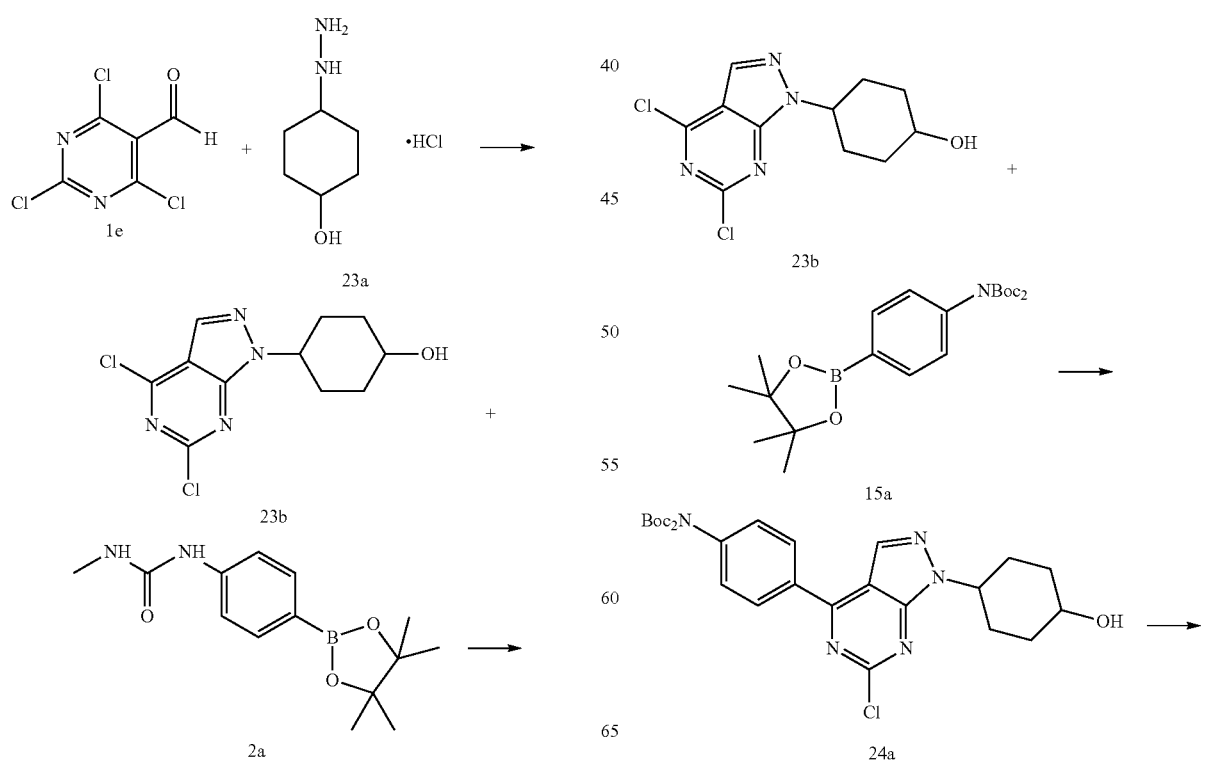

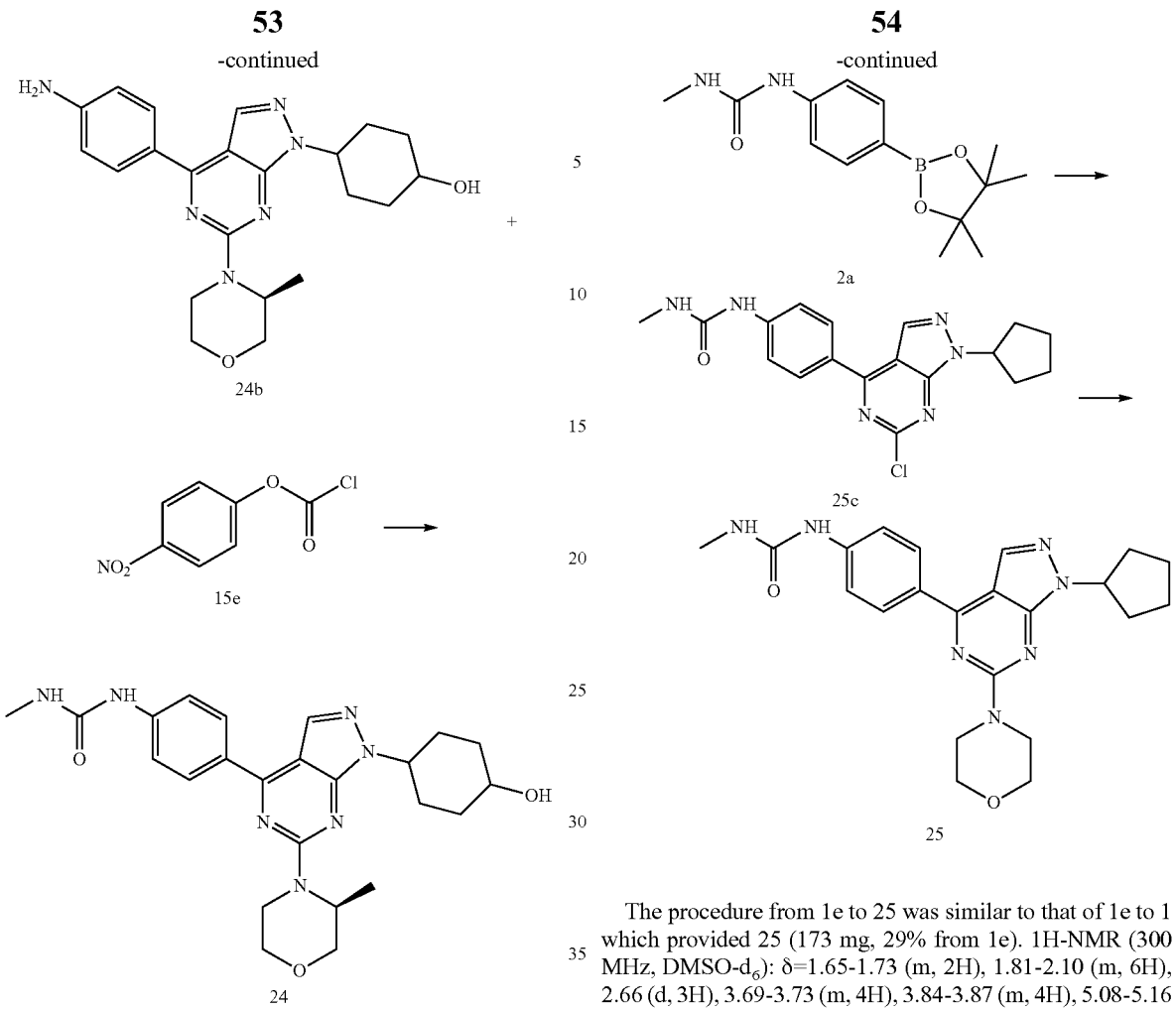

The procedure from 23b to 24 was similar to that of 1f to 17 which provided 24 (4 mg, 1.9% from 23b).

Example 24

N-[4-(1-cyclopentyl-6-morpholin-4-ylpyrazolo[4,5-e]pyrimidin-4-yl)phenyl](methylamino)carboxamide The procedure from 1e to 25 was similar to that of 1e to 1 which provided 25 (173 mg, 29% from 1e). 1H-NMR (300 MHz, DMSO-d$_6$): δ=1.65-1.73 (m, 2H), 1.81-2.10 (m, 6H), 2.66 (d, 3H), 3.69-3.73 (m, 4H), 3.84-3.87 (m, 4H), 5.08-5.16 (m, 1H), 6.14 (q, 1H), 7.61 (d, 2H), 8.18 (d, 2H), 8.36 (s, 1H), 8.92 (s, 1H). LC-MS [M+H]$^+$: 422.2.

Example 25

N-{4-[6-((3S)-3-methylmorpholin-4-yl)-1-cyclopentylpyrazolo[4,5-e]pyrimidin-4-yl]phenyl}(methylamino)carboxamide

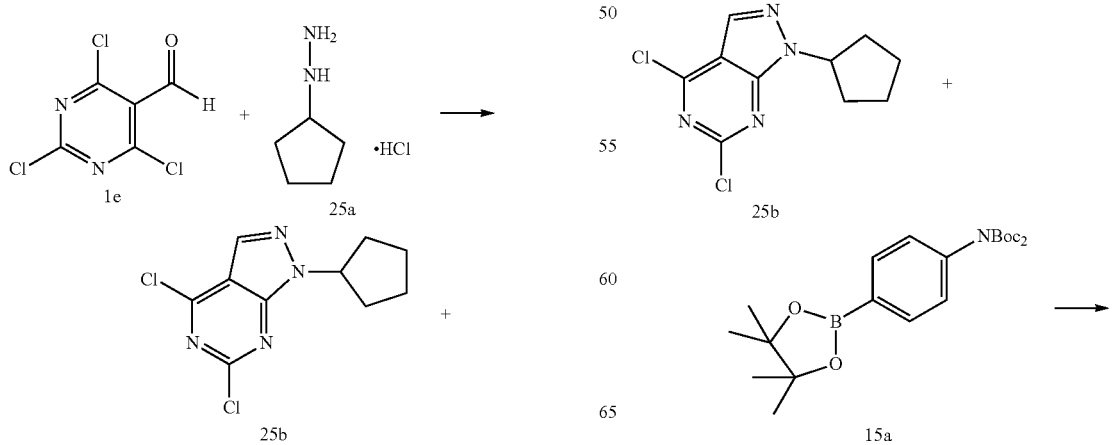

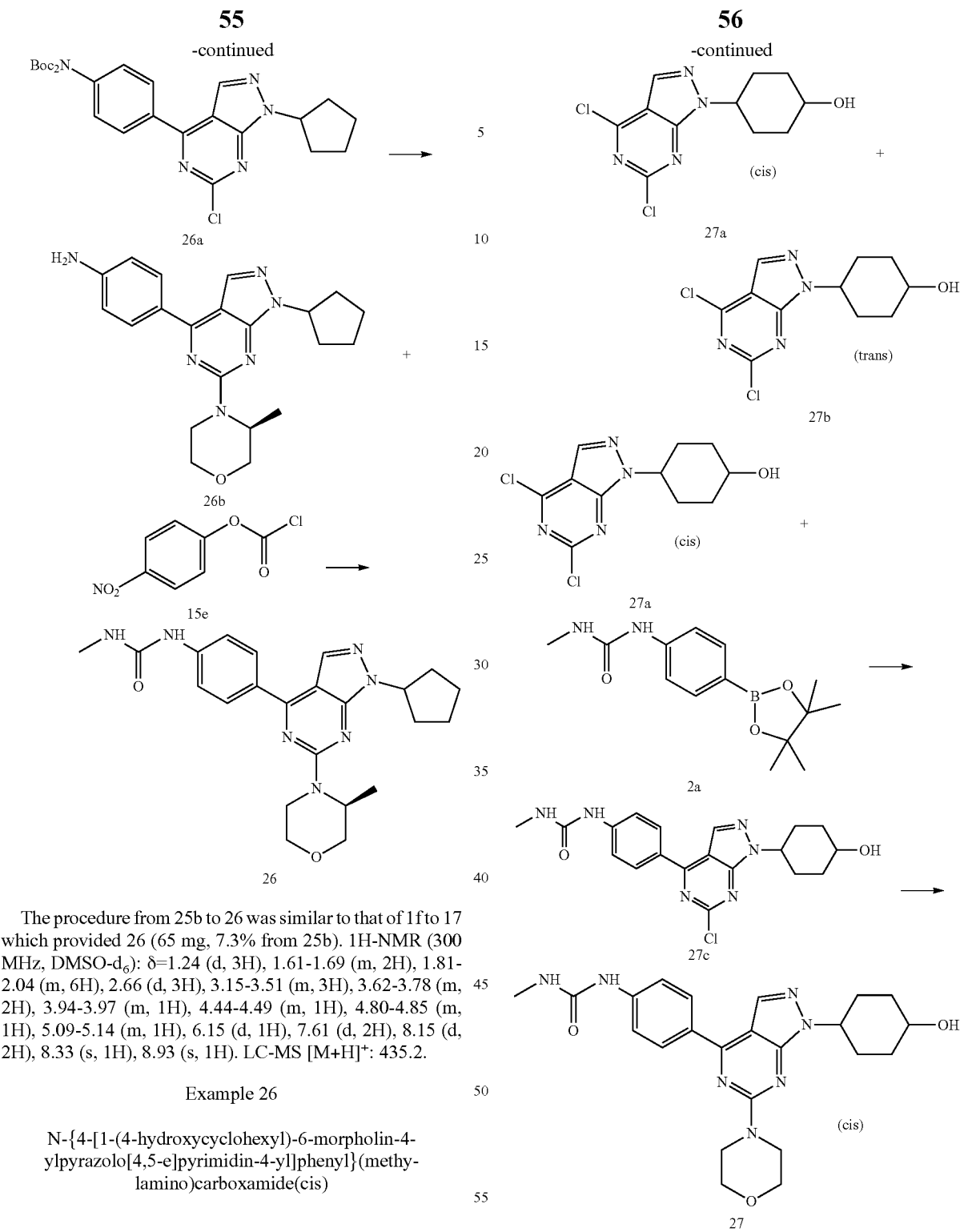

The procedure from 25b to 26 was similar to that of 1f to 17 which provided 26 (65 mg, 7.3% from 25b). 1H-NMR (300 MHz, DMSO-d$_6$): δ=1.24 (d, 3H), 1.61-1.69 (m, 2H), 1.81-2.04 (m, 6H), 2.66 (d, 3H), 3.15-3.51 (m, 3H), 3.62-3.78 (m, 2H), 3.94-3.97 (m, 1H), 4.44-4.49 (m, 1H), 4.80-4.85 (m, 1H), 5.09-5.14 (m, 1H), 6.15 (d, 1H), 7.61 (d, 2H), 8.15 (d, 2H), 8.33 (s, 1H), 8.93 (s, 1H). LC-MS [M+H]$^+$: 435.2.

Example 26

N-{4-[1-(4-hydroxycyclohexyl)-6-morpholin-4-ylpyrazolo[4,5-e]pyrimidin-4-yl]phenyl}(methylamino)carboxamide(cis)

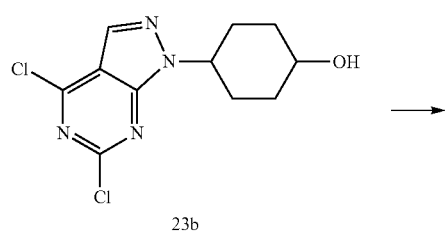

Step 1: 23b (120 mg, 0.42 mmol) was purified by Pre-TLC (PE: EA=8:1) to give 27a (39 mg, 32.5%) and 27b (73 mg, 60.8%).

Step 2: The procedure from 27a to 27 was similar to that of 23b to 23 which provided 27 (38 mg, 62% from 27a). 1H-NMR (300 MHz, DMSO-d$_6$): δ=1.59-1.67 (m, 4H), 1.79-1.84 (m, 2H), 2.27-2.41 (m, 2H), 2.67 (d, 3H), 3.71-3.74 (m, 4H), 3.85-3.88 (m, 4H), 4.47 (d, 1H), 4.53-4.64 (m, 1H), 6.14 (q, 1H), 7.60 (d, 2H), 8.17 (d, 2H), 8.36 (s, 1H), 8.92 (s, 1H). LC-MS [M+H]⁺: 452.2.

Example 27

N-{4-[1-(4-hydroxycyclohexyl)-6-morpholin-4-ylpyrazolo[4,5-e]pyrimidin-4-yl]phenyl}(methylamino)carboxamide(trans)

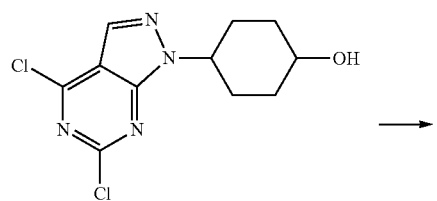
23b

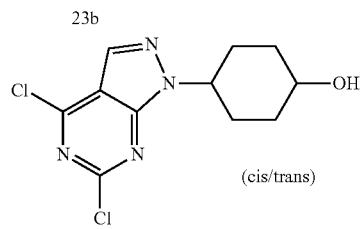
(cis/trans)
27a

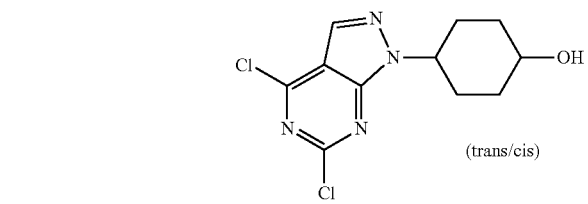
(trans/cis)
27b

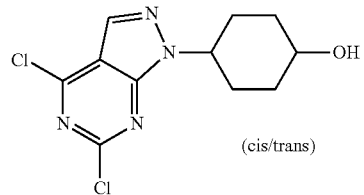
(cis/trans)
27a

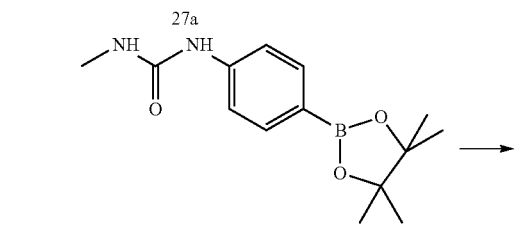
2a

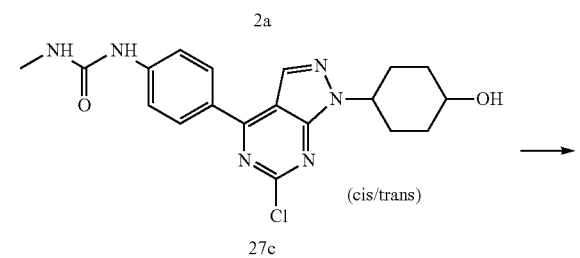
(cis/trans)
27c

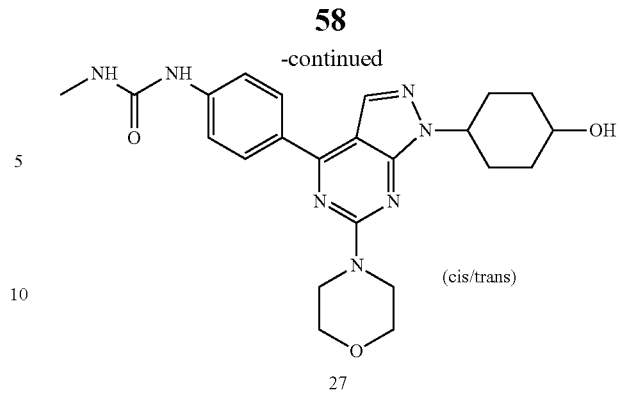
(cis/trans)
27

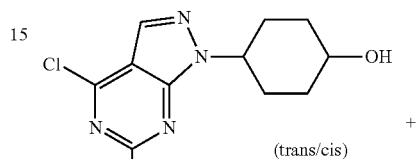
(trans/cis)
27b

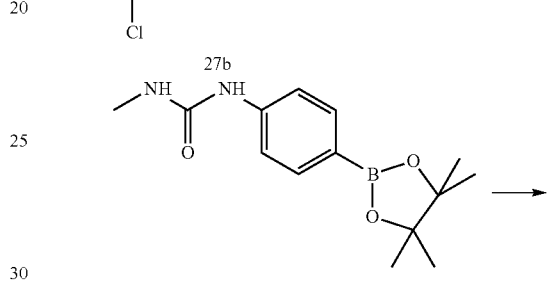
2a

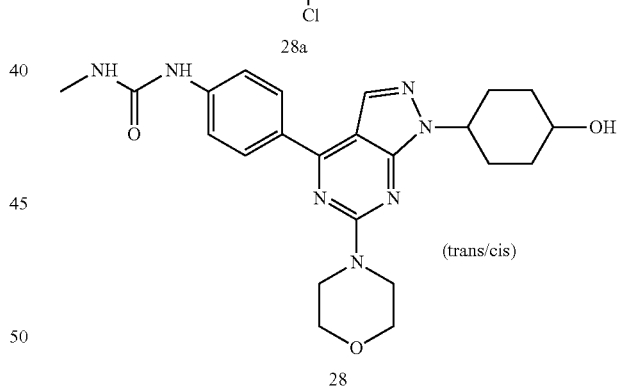
(trans/cis)
28

The procedure from 27b to 28 was similar to that of 23b to 23 which provided 28 (63 mg, 55% from 27b). 1H-NMR (300 MHz, DMSO-d₆): δ=1.32-1.46 (m, 2H), 1.84-2.07 (m, 6H), 2.67 (d, 3H), 3.49-3.56 (m, 1H), 3.70-3.74 (m, 4H), 3.83-3.87 (m, 4H), 4.51-4.58 (m, 1H), 4.68 (d, 1H), 6.13 (q, 1H), 7.60 (d, 2H), 8.16 (d, 2H), 8.34 (s, 1H), 8.92 (s, 1H). LC-MS [M+H]⁺: 452.2.

Biochemical Assay(example)

Assays are performed as described in Fabian et al. (2005) Nature Biotechnology, vol. 23, p. 329 and in Karaman et al. (2008) Nature Biotechnology, vol. 26, p. 127.

Kinase assays. For most assays, kinase-tagged T7 phage strains are grown in parallel in 24-well blocks in an *E. coli* host derived from the BL21 strain. *E. coli* are grown to logphase and are infected with T7 phage from a frozen stock (multiplicity of infection~0.1) and are incubated with shaking at 32° C. until lysis (~90 minutes). The lysates are centrifuged (6,000×g) and filtered (0.2 mm) to remove cell debris. The remaining kinases are produced in HEK-293 cells and subsequently tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (SeaBlock (Pierce), 1% BSA, 0.05% Tween 20, 1 mM DTT) to remove unbound ligand and to reduce non-specific phage binding. Binding reactions are assembled by combining kinases, liganded affinity beads, and test compounds in 1× binding buffer (20% SeaBlock, 0.17×PBS, 0.05% Tween 20, 6 mM DTT). Test compounds are prepared as 40× stocks in 100% DMSO and directly diluted into the assay. All reactions are performed in polypropylene 384-well plates in a final volume of 0.04 ml. The assay plates are incubated at room temperature with shaking for 1 hour and the affinity beads are washed with wash buffer (1×PBS, 0.05% Tween 20). The beads are then re-suspended in elution buffer (1×PBS, 0.05% Tween 20, 0.5 mM non-biotinylated affinity ligand) and are incubated at room temperature with shaking for 30 minutes. The kinase concentration in the eluates is measured by qPCR.

Compounds were tested using the above assay at Ambit Biosciences (San Diego, Calif., USA). Compounds of Examples 1, 2, 3, 6, 13, 15, 16, 17 showed $IC_{50}$ of less than 0.11 μM against mTOR, while their $IC_{50}$ against PI3K α, β, δ, γ are >0.1 μM.

Scintillation Proximity Assay (SPA) for p110α, p110β, p110γ, and PI3K C2β

GST-tagged bovine p110α, GST-tagged human p110β, His-tagged p110γ, and Glu-tagged PI3K C2β are expressed in an Sf9/Baculovirus system and purified as fusion proteins. The test compounds are dissolved in DMSO (0.5 μL) and each enzyme is mixed in 25 μL of buffer solution (p110α, β, γ assay: 20 mM Tris-HCl (pH 7.4), 160 mM NaCl, 2 mM dithiothreitol, 30 mM $MgCl_2$, 0.4 mM EDTA, 0.4 mM EGTA; PI3K C2β assay:

20 mM Tris-HCl (pH 7.4), 160 mM NaCl, 2 mM dithiothreitol, 5 mM $MgCl_2$, 15 mM $CaCl_2$, 0.4 mM EDTA). Then, 25 μL of 5 mM Tris-HCl supplemented with 1 μg PI (Sigma), 0.125 μCi [γ-$^{33}$P]ATP (Amersham Pharmacia), and 2 μM non-radiolabeled ATP (Sigma) are added to the mixture to initiate the reaction. After allowing the reaction to proceed at room temperature for 120 min, 0.2 mg of wheat germ agglutinin-coated SPA beads (Amersham) in 150 μL PBS is added. The mixture is left to stand for 5 min and then centrifuged at 300 g for 2 min. Radioactivity is measured using TopCount (Packard).

Cellular Assay:
Proliferation Assays

Cells (U87-MG, A375, HeLa, A549, MCF7, and MCF7 ADR-res) are cultured in DMEM with 10% fetal bovine serum and streptomycin/penicillin. Solutions of the test compounds (1 μL) are spotted onto a 96-well culture plate, followed by addition of cells (1×10$^4$) in 100 μL. After 46-h incubation, 10 μL of Alamar blue reagent is added to each well. After 2-h, the excitation/emission wavelengths at 544/590 nm are measured using Fluostar.

Compounds of Examples 1, 2, 9, 10, 11, 13, 14, 15, 20, 22, 23, 24, 25, 26, 27 showed $IC_{50}$ of less than 1 μM against proliferation of U87-MG and A549 cells.

I claim:
1. A compound of Formula II:

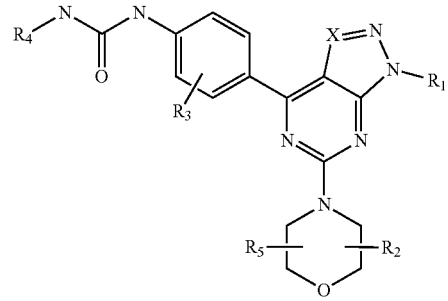

or a salt thereof; wherein X is CH;
$R_1$ is 1) heterocyclyl optionally substituted with $C(O)OR^{15}$, $C(O)R^{16}$, or $S(O)_2R^{17}$; or 2) cycloalkyl optionally substituted with OH, $C(O)OR^{15}$, or $R^{17}$;
$R_2$ is hydrogen or alkyl;
$R_3$ is hydrogen;
each $R_4$ is independently 1) alkyl; or 2) aryl optionally substituted with $R^{16}$ or $C(O)R^{16}$;
$R_5$ is hydrogen; or each $R_2$ and $R_5$ together with the atom(s) that each is respectively attached to can form a cyclo or heterocyclo structure;
$R^{15}$ is hydrogen or $C_1$-$C_4$ alkyl;
$R^{16}$ is heterocyclyl or $C_1$-$C_4$ alkyl, wherein each of said heterocyclyl or $C_1$-$C_4$ alkyl is independently optionally substituted with OH, halogen, $C_1$-$C_4$ alkyl, $C_1$-$C_4$ alkoxy, or $NH_2$; and
$R^{17}$ is $C_1$-$C_4$ alkyl optionally substituted with OH.

2. The compound of claim 1, wherein $R_2$ and $R_5$ together with the atoms to which they are attached form a heterocycloalkyl.

3. The compound of claim 1, wherein $R_1$ is heterocyclyl optionally substituted with $C(O)OR^{15}$, $C(O)R^{16}$, or $S(O)_2R^{17}$;
$R^{15}$ is hydrogen or $C_1$-$C_4$ alkyl;
$R^{16}$ is heterocyclyl or $C_1$-$C_4$ alkyl, wherein each of said heterocyclyl or $C_1$-$C_4$ alkyl is independently optionally substituted with OH, halogen, $C_1$-$C_4$ alkyl, $C_1$-$C_4$ alkoxy, or $NH_2$; and
$R^{17}$ is $C_1$-$C_4$ alkyl.

4. The compound of claim 1, wherein $R_1$ is cycloalkyl optionally substituted with OH, $C(O)OR^{15}$, or $R^{17}$;
$R^{15}$ is hydrogen or $C_1$-$C_4$ alkyl; and
$R^{17}$ is $C_1$-$C_4$ alkyl substituted with OH.

5. The compound of claim 1, wherein $R_4$ is alkyl.

6. The compound of claim 1, wherein $R_4$ is aryl optionally substituted with $R^{16}$ or $C(O)R^{16}$; and
$R^{16}$ is heterocyclyl or $C_1$-$C_4$ alkyl, wherein each of said heterocyclyl or $C_1$-$C_4$ alkyl is independently optionally substituted with OH, halogen, $C_1$-$C_4$ alkyl, $C_1$-$C_4$ alkoxy, or $NH_2$.

7. The compound of claim 1, wherein $R_4$ is aryl substituted with —$C(O)R^{16}$; and
$R^{16}$ is heterocyclyl or $C_1$-$C_4$ alkyl, wherein each of said heterocyclyl or $C_1$-$C_4$ alkyl is independently optionally substituted with OH, halogen, $C_1$-$C_4$ alkyl, $C_1$-$C_4$ alkoxy, or $NH_2$.

8. The compound of claim 7, wherein $R^{16}$ is heterocyclyl substituted with $C_1$-$C_4$ alkyl.

9. The compound of claim 1, wherein $R_4$ is aryl substituted with heterocyclyl.

10. The compound of claim 1, wherein;
$R_1$ is heterocyclyl optionally substituted with $C(O)OR^{15}$, $C(O)R^{16}$, or $S(O)_2 R^{17}$;
$R_4$ is alkyl;
$R^{15}$ is hydrogen or $C_1$-$C_4$ alkyl;
$R^{16}$ is heterocyclyl or $C_1$-$C_4$ alkyl, wherein each of said heterocyclyl or $C_1$-$C_4$ alkyl is independently optionally substituted with OH, halogen, $C_1$-$C_4$ alkyl, $C_1$-$C_4$ alkoxy, or $NH_2$; and
$R^{17}$ is alkyl.

11. The compound of claim 1, wherein the compound is one of methyl 4-[4-[4-(methylcarbamoylamino)phenyl]-6-morpholino-pyrazolo[3,4-d]pyrimidin-1-yl]piperidine-1-carboxylate;

- 1-methyl-3-[4-[1-[1-(4-methylpiperazine-1- carbonyl)-4-piperidyl]-6-morpholino-pyrazolo[3,4-d]pyrimidin-4-yl]phenyl]urea;
- 1-[4-[1-[1-[(2S)-2-aminopropanoyl]-4-piperidyl]-6-morpholino-pyrazolo[3,4-d]pyrimidin-4-yl]phenyl]-3-methyl-urea;
- 1-[4-[1-[1-(2-hydroxyacetyl)-4-piperidyl]-6-morpholino-pyrazolo[3,4-d]pyrimidin-4-yl]phenyl]-3-methyl-urea;
- 1-[4-[1-[1-[(2S)-2-hydroxypropanoyl]-4-piperidyl]-6-morpholino-pyrazolo[3,4-d]pyrimidin-4-yl]phenyl]-3-methylurea;
- 1-[4-[1-[1-(2-methoxyacetyl)-4-piperidyl]-6-morpholino-pyrazolo[3,4-d]pyrimidin-4-yl]phenyl]-3-methyl-urea;
- 1-methyl-3-[4-[1-(1-methylsulfonyl-4-piperidyl)-6-morpholino-pyrazolo[3,4-d]pyrimidin-4-yl]phenyl]urea;
- 1-methyl-3-[4-(6-morpholino-1-tetrahydropyran-4-yl-pyrazolo[3,4-d]pyrimidin-4-yl)phenyl]urea;
- 1-methyl-3-[4-[6-(8-oxa-3-azabicyclo[3.2.1]octan-3-yl)-1-tetrahydropyran-4-yl-pyrazolo[3,4-d]pyrimidin-4-yl]phenyl]urea;
- 1-methyl-3-[4-[6-[(3S)-3-methylmorpholin-4-yl]-1-tetrahydropyran-4-yl-pyrazolo[3,4-d]pyrimidin-4-yl]phenyl]urea;
- N-{4-[1-(2H-3,4,5,6-tetrahydropyran-4-yl)-6-((3R)-3-methylmorpholin-4-yl)pyrazolo[4,5-e]pyrimidin-4-yl]phenyl}(methylamino)carboxamide;
- ethyl 4-(4-{4-[(methylamino)carbonylamino]phenyl}-6-morpholin-4-yl pyrazolo[5,4-d]pyrimidinyl)cyclohexanecarboxylate;
- N-(4-{1-[4-(hydroxymethyl)cyclohexyl]-6-morpholin-4-ylpyrazolo[4,5-e]pyrimidin-4-yl}phenyl)(methylamino)carboxamide;
- 4-(4-{4-[(methylamino)carbonylamino]phenyl}-6-morpholin-4-yl pyrazolo[5,4-d]pyrimidinyl)cyclohexanecarboxylic acid;
- N-{4-[1-(4-hydroxycyclohexyl)-6-morpholin-4-ylpyrazolo[4,5-e]pyrimidin-4-yl]phenyl}(methylamino)carboxamide;
- 4-[6-((3S)-3-methylmorpholin-4-yl)-4-(4-aminophenyl)pyrazolo[5,4-d]pyrimidinyl]cyclohexan-1-ol;
- N-[4-(1-cyclopentyl-6-morpholin-4-ylpyrazolo[4,5-e]pyrimidin-4-yl) phenyl](methylamino)carboxamide;
- N-{4-[6-((3S)-3-methylmorpholin-4-yl)-1-cyclopentylpyrazolo[4,5-e]pyrimidin-4-yl]phenyl}(methylamino)carboxamide;
- N-{4-[1-(4-hydroxycyclohexyl)-6-morpholin-4-ylpyrazolo[4,5-e]pyrimidin-4-yl]phenyl}(methylamino)carboxamide(cis);
- N-{4-[1-(4-hydroxycyclohexyl)-6-morpholin-4-ylpyrazolo[4,5-e]pyrimidin-4-yl]phenyl}(methylamino)carboxamide(trans);
- 1-[4-(6-morpholino-1-tetrahydropyran-4-yl-pyrazolo[3,4-d]pyrimidin-4-yl)phenyl]-3-(2,2,2-trifluoroethyl) urea;
- 1-[4-[6-[(3S)-3-methylmorpholin-4-yl]-1-tetrahydropyran-4-yl-pyrazolo[3,4-d]pyrimidin-4-yl]phenyl]-3-(2,2,2-trifluoroethyl)urea.

* * * * *